US012796989B2

(12) United States Patent
Cappato

(10) Patent No.: US 12,796,989 B2
(45) Date of Patent: Nov. 17, 2026

(54) SYSTEM AND METHOD FOR DEPLOYING A RETRIEVABLE, SELF-EXPANDABLE STENT ASSEMBLY

(71) Applicant: Riccardo Cappato, Milan (IT)

(72) Inventor: Riccardo Cappato, Milan (IT)

( * ) Notice: Subject to any disclaimer, the term of this patent is extended or adjusted under 35 U.S.C. 154(b) by 314 days.

(21) Appl. No.: 18/614,523

(22) Filed: Mar. 22, 2024

(65) Prior Publication Data

US 2025/0295344 A1 Sep. 25, 2025

(51) Int. Cl.

| | |
|---|---|
| ***A61B 5/00*** | (2006.01) |
| ***A61B 5/251*** | (2021.01) |
| ***A61B 5/273*** | (2021.01) |
| ***A61B 5/287*** | (2021.01) |
| ***A61F 2/95*** | (2013.01) |

(52) U.S. Cl.

CPC ............ *A61B 5/287* (2021.01); *A61B 5/0006* (2013.01); *A61B 5/251* (2021.01); *A61B 5/273* (2021.01); *A61F 2/95* (2013.01); *A61B 2560/0468* (2013.01); *A61B 2560/066* (2013.01); *A61B 2562/046* (2013.01); *A61F 2002/9505* (2013.01)

(58) Field of Classification Search

None

See application file for complete search history.

(56) References Cited

U.S. PATENT DOCUMENTS

| | | | |
|---|---|---|---|
| 4,649,924 | A | 3/1987 | Taccardi |
| 4,699,147 | A | 10/1987 | Chilson et al. |
| 5,697,377 | A | 12/1997 | Wittkampf |
| 5,718,241 | A | 2/1998 | Ben-Haim et al. |

(Continued)

FOREIGN PATENT DOCUMENTS

| | | |
|---|---|---|
| AU | 2017276276 | 12/2017 |
| AU | 2019283829 | 12/2019 |

(Continued)

OTHER PUBLICATIONS

Annotated Werneth Fig 2 (Year: 2026).*

Nademanee, K., M.D., Faac, et al., "A New Approach for Catheter Ablation of Atrial Fibrillation: Mapping of the Electrophysiologic Substrate". Journal of the American College of Cardiology, 2004, vol. 43, No. 11.

(Continued)

*Primary Examiner* — Michael F Peffley
*Assistant Examiner* — Nicholas S Borsch
(74) *Attorney, Agent, or Firm* — ROEDER & BRODER LLP; James P. Broder

(57) ABSTRACT

A method for deploying a locator assembly (500) in or near a heart (101) includes coupling a plurality of electrodes (102) to a device body (512) to form at least a portion of the locator assembly (500), the device body (512) including a self-expandable stent; positioning the device body (512) within an inner cavity (523A) of a sheath (523); inserting the locator assembly (500) within the heart (101); generating relative movement between the locator assembly (500) and the sheath (523) so that at least a portion of the device body (512) is no longer positioned within the inner cavity (523A); receiving electrical signals from the heart (101) with the plurality of electrodes (102); and determining a location of arrhythmogenic foci (732) with the locator assembly (500) based at least in part on the electrical signals received from the heart (101), the device body (512) remaining engaged with the inner cavity (523A) of the sheath (523) while the locator assembly (500) is being used to determine the location of the arrhythmogenic foci (732).

18 Claims, 9 Drawing Sheets

(56) References Cited

U.S. PATENT DOCUMENTS

| | | | |
|---|---|---|---|
| 6,500,174 | B1 | 12/2002 | Maguire et al. |
| 6,947,785 | B1 | 9/2005 | Beatty et al. |
| 6,978,168 | B2 | 12/2005 | Beatty et al. |
| 6,990,370 | B1 | 1/2006 | Beatty et al. |
| 7,195,628 | B2 | 3/2007 | Falkenberg |
| 7,907,994 | B2 | 3/2011 | Stolarski et al. |
| 8,364,235 | B2 | 1/2013 | Kordis et al. |
| 8,644,927 | B2 | 2/2014 | Imran |
| 9,119,533 | B2 | 9/2015 | Ghaffari |
| 9,138,160 | B2 | 9/2015 | Imran |
| 9,289,132 | B2 | 3/2016 | Ghaffari et al. |
| 9,629,567 | B2 | 4/2017 | Porath et al. |
| 9,662,069 | B2 | 5/2017 | De Graff et al. |
| 9,687,166 | B2 | 6/2017 | Subramaniam et al. |
| 9,764,142 | B2 | 9/2017 | Imran |
| 9,861,433 | B2 | 1/2018 | Tegg |
| 9,894,756 | B2 | 2/2018 | Weinkam et al. |
| 9,974,963 | B2 | 5/2018 | Imran |
| 9,974,970 | B2 | 5/2018 | Nuta et al. |
| 10,136,829 | B2 | 11/2018 | Deno et al. |
| 10,194,994 | B2 | 2/2019 | Deno et al. |
| 10,537,287 | B2 | 1/2020 | Braido et al. |
| 10,549,092 | B1 | 2/2020 | Hakki |
| 10,575,783 | B2 | 3/2020 | Oxley |
| 10,722,240 | B1 | 7/2020 | Melanson |
| 10,894,167 | B2 | 1/2021 | Koop et al. |
| 11,013,554 | B2 | 5/2021 | Coates |
| 11,093,038 | B2 | 8/2021 | Yoo |
| 11,550,391 | B2 | 1/2023 | Yoo et al. |
| 11,625,014 | B2 | 4/2023 | Oxley et al. |
| 11,630,517 | B1 | 4/2023 | Yoo et al. |
| 11,672,986 | B2 | 6/2023 | Opie et al. |
| 11,755,110 | B2 | 9/2023 | Yoo |
| 11,883,671 | B2 | 1/2024 | Opie et al. |
| 2003/0018362 | A1* | 1/2003 | Fellows ............. A61B 18/1492 607/5 |
| 2003/0050637 | A1 | 3/2003 | Maguire |
| 2003/0176816 | A1 | 9/2003 | Maguire |
| 2005/0010095 | A1 | 1/2005 | Stewart et al. |
| 2005/0273014 | A1 | 12/2005 | Gianchandani et al. |
| 2005/0277839 | A1 | 12/2005 | Alderman et al. |
| 2006/0089637 | A1* | 4/2006 | Werneth ................. A61B 18/16 606/41 |
| 2006/0200039 | A1 | 9/2006 | Brockway et al. |
| 2006/0241733 | A1 | 10/2006 | Zhang et al. |
| 2008/0039904 | A1 | 2/2008 | Bulkes |
| 2008/0077184 | A1 | 3/2008 | Denker |
| 2009/0192405 | A1 | 7/2009 | Carney |
| 2009/0192495 | A1 | 7/2009 | Ostrovsky et al. |
| 2010/0063562 | A1 | 3/2010 | Cowan |
| 2010/0179632 | A1 | 7/2010 | Bruszewski et al. |
| 2010/0191089 | A1 | 7/2010 | Stebler et al. |
| 2012/0197150 | A1 | 8/2012 | Cao et al. |
| 2013/0253347 | A1 | 9/2013 | Griswold et al. |
| 2014/0257463 | A1* | 9/2014 | Sweeney ............... A61F 2/2475 623/1.24 |
| 2014/0277310 | A1* | 9/2014 | Beetel .................. A61N 1/0551 607/116 |
| 2014/0288667 | A1 | 9/2014 | Oxley |
| 2015/0065945 | A1 | 3/2015 | Zarins |
| 2015/0141764 | A1 | 5/2015 | Harks et al. |
| 2016/0038087 | A1 | 2/2016 | Hunter |
| 2016/0235999 | A1 | 8/2016 | Nuta |
| 2016/0287174 | A1 | 10/2016 | Joseph |
| 2016/0351292 | A1 | 12/2016 | Toth |
| 2017/0042615 | A1 | 2/2017 | Salahieh |
| 2018/0049877 | A1 | 2/2018 | Venkatasubramanian |
| 2018/0092763 | A1 | 4/2018 | Dagan et al. |
| 2018/0132754 | A1 | 5/2018 | Kusumoto |
| 2018/0272121 | A1 | 9/2018 | Yankelson |
| 2019/0175111 | A1 | 6/2019 | Genereux et al. |
| 2019/0175372 | A1 | 6/2019 | Boyden et al. |
| 2019/0232066 | A1 | 8/2019 | Lim et al. |
| 2019/0328259 | A1 | 10/2019 | Deno et al. |
| 2019/0388002 | A1 | 12/2019 | Bozsak et al. |
| 2020/0016396 | A1 | 1/2020 | Yoo |
| 2020/0363869 | A1 | 11/2020 | Yoo |
| 2021/0373665 | A1 | 12/2021 | Yoo |
| 2021/0378595 | A1 | 12/2021 | Oxley |
| 2022/0039730 | A1 | 2/2022 | Ravuna et al. |
| 2022/0240833 | A1 | 8/2022 | Oxley |
| 2022/0253024 | A1 | 8/2022 | Oxley et al. |
| 2022/0369994 | A1 | 11/2022 | Oxley |
| 2023/0101497 | A1 | 3/2023 | Werneth |
| 2023/0107850 | A1 | 4/2023 | Yoo et al. |
| 2023/0121587 | A1 | 4/2023 | Cappato |
| 2023/0218198 | A1 | 7/2023 | Bennett et al. |
| 2023/0244314 | A1 | 8/2023 | Oxley et al. |
| 2023/0288987 | A1 | 9/2023 | Yoo et al. |
| 2023/0302282 | A1 | 9/2023 | Opie et al. |
| 2023/0350360 | A1 | 11/2023 | Oxley et al. |
| 2023/0389851 | A1 | 12/2023 | Tal et al. |
| 2024/0019933 | A1 | 1/2024 | Yoo |
| 2025/0319317 | A1 | 10/2025 | Cappato |

FOREIGN PATENT DOCUMENTS

| | | |
|---|---|---|
| CA | 3144083 | 11/2020 |
| CN | 104023787 | 7/2017 |
| CN | 107374623 | 11/2017 |
| CN | 114144748 | 3/2022 |
| CN | 115052657 | 9/2022 |
| CN | 115698906 | 2/2023 |
| EP | 3536375 | 11/2019 |
| EP | 3576618 A1 | 12/2019 |
| EP | 3969991 | 3/2022 |
| EP | 4051374 | 9/2022 |
| JP | A2006130064 | 5/2006 |
| JP | A2008237882 | 10/2008 |
| JP | 6149269 | 6/2017 |
| JP | 2017159079 | 9/2017 |
| JP | A2020529879 | 10/2020 |
| JP | A2021505353 | 2/2021 |
| JP | A2021069921 | 5/2021 |
| JP | 2022533090 | 7/2022 |
| JP | 2023501446 | 1/2023 |
| JP | 2023519968 | 5/2023 |
| KR | 20160090877 A | 8/2016 |
| KR | 20220030935 | 3/2022 |
| KR | 20230019403 | 2/2023 |
| WO | WO0069334 | 11/2000 |
| WO | WO0069334 A1 | 11/2000 |
| WO | WO2017137077 | 11/2007 |
| WO | WO2010042653 A1 | 4/2010 |
| WO | WO2012025245 A1 | 3/2012 |
| WO | WO2013049887 A1 | 4/2013 |
| WO | WO2014177634 A1 | 11/2014 |
| WO | WO2017070252 A1 | 4/2017 |
| WO | WO2018185256 A1 | 10/2018 |
| WO | WO2020227774 | 11/2020 |
| WO | WO2021086972 | 5/2021 |
| WO | WO2021092462 | 5/2021 |
| WO | WO2021097448 | 5/2021 |
| WO | WO2021202915 | 10/2021 |
| WO | WO2023137396 | 7/2023 |
| WO | WO2023137427 | 7/2023 |
| WO | WO2023147233 | 8/2023 |
| WO | WO2023240043 | 12/2023 |
| WO | WO2024006998 | 1/2024 |
| WO | WO2025215590 A1 | 10/2025 |

OTHER PUBLICATIONS

Meng, S., et al., "Accurate recovery of atrial endocardial potential maps from non-contact electrode data". Auckland Bioengineering Institute, The University of Auckland, New Zealand.

Shariat, M.H., et al. "Localization of the Ectopic Spiral Electrial Source Using Intracardiac Electrograms During Atrial Fibrillation". Proceeding of the IEEE 28th, Canadian Conference on Electrical and Computer Engineering, Halifax, Canada, May 3-6, 2015.

Jiang, R., Md., et al., "Multielectrode Catheter for Substrate Mapping for Scar-Related VT Ablation: A Comparison between Grid

(56) References Cited

OTHER PUBLICATIONS versus Linear Configurations". At the Forefront UChicago Medicine; Center for Arrhythmia Care; Heart and Vascular Center; Chicago, IL.
Calkins, H., "Three Dimensional Mapping of Atrial Fibrillation: Techniques and Necessity". Journal of Interventional Cardiac Electrophysiology 13, 53-59, 2005.
Shariat, M.H., "Processing the Intracardiac Electrogram for Atrial Fibrillation Ablation". Queen's University, Kingston, Ontario, Canada, Sep. 2016.
Sacher, F., et al. "Comparison of Manual vs. Automatic Annotation to Identify Abnormal Substrate for Scar Related VT Ablation". CHU, University of Bordeaux.
"Reveal LINQ LNQ11, Insertable Cardiac Monitor", Clinician Manual. Medtronic, Inc. 2015.
Invitation to Pay Additional Fees and Annex Communication Relating to the Results of the Partial International Search issued by the European Patent Office as ISA, on Jan. 25, 2023, in Application Serial No. PCT/IB2022/059700.
Gardner J., "Moving with the Power of Thought", https://pursuit.unimelb.edu.au/articles/moving-with-the-power-of-thought. Feb. 9, 2016.
Hodsen, S., "DARPA: Minimally Invasive Implant Could Unlock Thought-Controlled Prosthetics", https://www.meddeviceonline.com/doc/darpa-minimally-invasive-implant-could-unlock-thought-controlled-prosthetics-0001. Feb. 24, 2016.
Synchron https://synchron.com/ accessed on Oct. 17, 2022.
International Search Report and Written Opinion, issued by ISA European Patent Office, Aug. 4, 2025, in Application Serial No. PCT/IB2025/053801. (related .02PCT).

* cited by examiner

SYSTEM AND METHOD FOR DEPLOYING A RETRIEVABLE, SELF-EXPANDABLE STENT ASSEMBLY

BACKGROUND

Atrial fibrillation is an irregular and sometimes rapid heart rate that can increase the risk of stroke, heart failure, and other heart-related complications. During atrial fibrillation, the heart's two upper chambers (the atria) beat chaotically and irregularly-out of coordination with the heart's two lower chambers (the ventricles). Atrial fibrillation symptoms often include heart palpitations, shortness of breath, and weakness. Although atrial fibrillation usually isn't life-threatening, it is a severe medical condition that sometimes requires treatment. Atrial fibrillation can originate from focal sources (referred to herein as "arrhythmogenic foci") in the atria or other locations in and around the heart.

Catheter ablation of atrial fibrillation is currently performed using an anatomically-based approach to the atrial substrate. Previous models hypothesize that most clinical atrial fibrillation episodes originate inside the pulmonary veins. Eligible patients for atrial fibrillation ablation are not representative of the typical patient with atrial fibrillation (e.g., eligible patients for atrial fibrillation ablation on average are ten years younger, commonly with fewer co-morbidities). As a result, pulmonary vein isolation is unlikely to be an effective strategy to cure atrial fibrillation in the overall population of atrial fibrillation patients.

The anatomically-based approach to the atrial substrate surrogates the ability of clinicians to provide relevant electrophysiological information during clinical episodes of atrial fibrillation. Problems with the anatomically-based approach include (1) recurrent conduction across the isolating ablation lesions deployed at the pulmonary vein orifice/antrum, and (2) precipitation of atrial fibrillation events from sites other than the pulmonary vein. Recurrence of atrial fibrillation events includes many patients among those in whom pulmonary vein isolation fails to control recurrences of atrial fibrillation. In all patients with previously successful pulmonary vein isolation, recurrent episodes still exist.

Mapping areas alternative to pulmonary veins that generate extra beats precipitating atrial fibrillation episodes is currently precluded by the inability to monitor real-time precipitating episodes. Other approaches, such as a surrogate strategy to real-time mapping, are represented by catecholamine-induced atrial fibrillation during ablation procedures. However, the surrogate strategy is not standardized, is time-consuming and is largely ineffective (as drug-induced atrial fibrillation does not represent spontaneous atrial fibrillation). Another major problem is the ability to accurately determine the precise location of the arrhythmogenic foci that is causing atrial fibrillation. Thus, it is desired to develop an effective system and method for accurately determining the precise location of the arrhythmogenic foci that is actually causing the atrial fibrillation.

SUMMARY

The present invention is directed toward a method for deploying a locator assembly in or near a heart. In various embodiments, the method includes the steps of coupling a plurality of electrodes to a device body to form at least a portion of the locator assembly, the device body including a self-expanding stent; positioning the device body with the plurality of electrodes coupled thereto within an inner cavity of a sheath; inserting the locator assembly within the heart while the device body is positioned within the inner cavity of the sheath; generating relative movement between the locator assembly and the sheath so that at least a portion of the device body is no longer positioned within the inner cavity of the sheath, the device body being engaged with the inner cavity of the sheath when the at least a portion of the device body is no longer positioned within the inner cavity of the sheath; receiving electrical signals from the heart with the plurality of electrodes of the locator assembly; and determining a location of arrhythmogenic foci in or near the heart with the locator assembly based at least in part on the electrical signals received from the heart by the plurality of electrodes, the device body remaining engaged with the inner cavity of the sheath while the locator assembly is being used to determine the location of the arrhythmogenic foci.

In some embodiments, the method further includes the step of tethering the device body to the sheath with a tethering system so that the device body is tethered to the sheath when the at least a portion of the device body is no longer positioned within the inner cavity of the sheath, the tethering system being coupled to the device body and extending into the sheath.

In certain embodiments, the step of generating includes generating relative movement between the locator assembly and the sheath so that an entirety of the device body is no longer positioned within the inner cavity of the sheath.

In some embodiments, the step of tethering includes the device body being tethered to the sheath with the tethering system when the entirety of the device body is no longer positioned within the inner cavity of the sheath.

In certain embodiments, the step of tethering includes coupling one or more tethering wires to the device body, and extending the one or more tethering wires into the sheath.

In various embodiments, the method further includes the step of inhibiting the device body from being fully removed from the inner cavity of the sheath with a removal inhibitor.

In some embodiments, the step of generating includes the at least a portion of the device body being configured to spontaneously move from a contracted state to an expanded state when the at least a portion of the device body is no longer positioned within the inner cavity of the sheath.

In certain embodiments, the step of positioning includes the sheath being configured to maintain the device body in the contracted state while the device body is positioned within the inner cavity of the sheath.

In various embodiments, the method further includes the step of subsequently generating relative movement between the locator assembly and the sheath so that the at least a portion of the device body is moved back within the inner cavity of the sheath and the at least a portion of the device body moves from the expanded state back into the contracted state.

In some embodiments, the method further includes the step of removing the locator assembly from within the heart while the device body is positioned back within the inner cavity of the sheath.

In certain embodiments, the step of coupling the plurality of electrodes includes positioning at least two of the plurality of electrodes circumferentially about the device body; and positioning at least two of the plurality of electrodes longitudinally along the device body.

In various embodiments, the method further includes the steps of electrically coupling the device body to an external device with one or more wires; and transmitting information and data from the locator assembly to the external device via the one or more wires.

In some embodiments, the method further includes the steps of coupling a communicator to the device body; electrically coupling the device body to an external device with the communicator; and wirelessly transmitting information and data from the locator assembly to the external device via the communicator.

The present invention is also directed toward a locator system configured for deployment in or near a heart, including a deployment catheter including a sheath that defines an inner cavity therein; and a locator assembly including (i) a device body including a self-expanding stent that is configured to be positioned within and engage the heart, the device body being positioned within the inner cavity of the sheath while the device body is being positioned within the heart; and (ii) a plurality of electrodes that are coupled to the device body, the plurality of electrodes being configured to receive electrical signals from the heart to determine a location of arrhythmogenic foci in or near the heart; wherein relative movement between the locator assembly and the sheath is generated so that at least a portion of the device body is no longer positioned within the inner cavity of the sheath during a procedure when the locator assembly is being used to determine the location of the arrhythmogenic foci, the device body being engaged with the inner cavity of the sheath when the at least a portion of the device body is no longer positioned within the inner cavity of the sheath; and wherein the locator assembly remains engaged with the inner cavity of the sheath during the procedure when the locator assembly is being used to determine the location of the arrhythmogenic foci.

The present invention is further directed toward a method for deploying a locator assembly in or near a heart, including the steps of coupling a plurality of electrodes to a device body to form at least a portion of the locator assembly, the device body including a self-expanding stent; positioning the device body with the plurality of electrodes coupled thereto within an inner cavity of a sheath, the sheath being configured to maintain the device body in a contracted state while the device body is positioned within the inner cavity of the sheath; inserting the locator assembly within the heart while the device body is positioned within the inner cavity of the sheath; generating relative movement between the locator assembly and the sheath so that at least a portion of the device body is no longer positioned within the inner cavity of the sheath, the device body being engaged with the inner cavity of the sheath when the at least a portion of the device body is no longer positioned within the inner cavity of the sheath, the at least a portion of the device body being configured to spontaneously move from the contracted state to an expanded state when the at least a portion of the device body is no longer positioned within the inner cavity of the sheath, the device body being engaged with the inner cavity of the sheath via one of (i) a tethering system including one or more tethering wires that are coupled to the device body and extend into the sheath, and (ii) a removal inhibitor that inhibits the device body from being fully removed from the inner cavity of the sheath; receiving electrical signals from the heart with the plurality of electrodes of the locator assembly; determining a location of arrhythmogenic foci in or near the heart with the locator assembly based at least in part on the electrical signals received from the heart by the plurality of electrodes, the device body remaining engaged with the inner cavity of the sheath while the locator assembly is being used to determine the location of the arrhythmogenic foci; subsequently generating relative movement between the locator assembly and the sheath so that the at least a portion of the device body is moved back within the inner cavity of the sheath and the at least a portion of the device body moves from the expanded state back into the contracted state; and removing the locator assembly from within the heart while the device body is positioned back within the inner cavity of the sheath.

This summary is an overview of some of the teachings of the present invention and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1A:
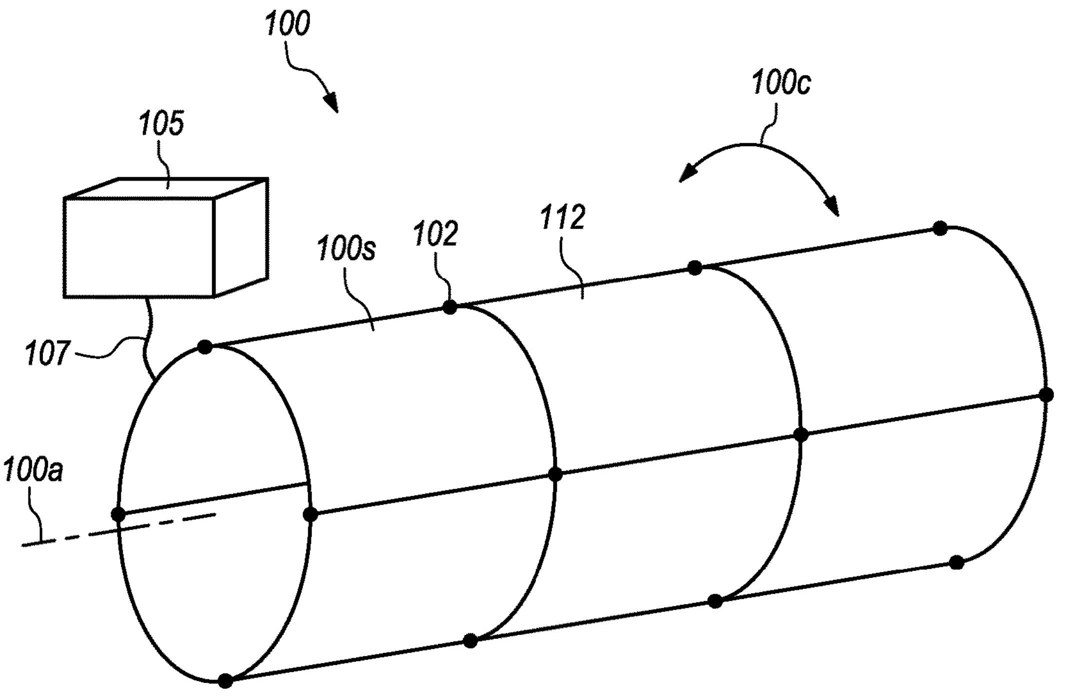
FIG. 1A is a simplified perspective view of an embodiment of a locator assembly for locating arrhythmogenic foci in or near a heart and an external device, the locator assembly having features of the present invention.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

The present invention is directed toward systems and methods for deploying a stent assembly (also sometimes referred to herein as a "locator assembly" and/or "stent"), in a vessel within a body of a patient. In certain embodiments, the noted devices can be used for determining the location of arrhythmogenic foci, and are configured to enable mapping of precipitating episodes of clinical atrial fibrillation during a patient's daily life. In particular, in such embodiments, a locator assembly 100 can be implanted and/or positioned within the patient so that the locator assembly 100 can locate the origin of clinical atrial fibrillation in or near a heart 101 of the patient. As used herein, the "heart" is understood to mean the heart including both atrial chambers, both ventricular chambers, the septum, the pulmonary veins, the coronary sinus, the fossa ovalis, the superior vena cava, the inferior vena cava, the muscular sleeves, the vascular walls, connected, electrically active tissues, and all other heart support structures in or near the heart.

The locator assembly 100 can be deployed and used in the systems and methods described herein for determining a location of arrhythmogenic foci 732 (illustrated in FIG. 7, for example) in or near the heart 101 of the patient. The systems, methods, and devices for determining the location of the arrhythmogenic foci 732 in or near the heart 101 described herein can vary.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention, as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming but would nevertheless be a routine undertaking of engineering for those of ordinary skill in the art having the benefit of this disclosure.

FIG. 1A is a simplified perspective view of an embodiment of a locator assembly 100 having features of the present invention that is utilized for locating arrhythmogenic foci 732 (illustrated in FIG. 7) in or near the heart 101 (illustrated in FIG. 1B), and an external device 105 that is configured to communicate with the locator assembly 100. More particularly, as described, the locator assembly 100 is configured to generate and/or collect information and data for purposes of locating the arrhythmogenic foci 732 in or near the heart 101, and then such information and data is transmitted to the external device 105, such as by a wired connection or a wireless connection, for any necessary or desired processing.

As provided herein, the locator assembly 100 is deliverable to and/or positionable within a portion of the heart 101 of a patient for performing a diagnostic procedure of locating the arrhythmogenic foci 732 in or near the heart 101. For example, in certain implementations, the locator assembly 100 can be delivered to and/or positioned within a coronary sinus 127 (illustrated in FIG. 1B) of the heart 101 (and near a vena cordis media 128 (illustrated in FIG. 1B) of the heart 101) for purposes of locating the arrhythmogenic foci 732. Alternatively, in other implementations, the locator assembly 100 can be delivered to and/or positioned within other portions of the heart 101 for purposes of locating the arrhythmogenic foci 732. The locator assembly 100 can map precipitating episodes of clinical atrial fibrillation during the patient's daily life.

The locator assembly 100 can vary depending on its design requirements. In the embodiment illustrated in FIG. 1A, the locator assembly 100 can include a device body 112, and a plurality of electrodes 102 (only one electrode is identified, with other electrodes shown as black dots in FIG. 1A, FIGS. 2A-2B, and FIGS. 3-4) that are coupled and/or secured to the device body 112. As used herein, "components" of the locator assembly 100 can include at least the plurality of electrodes 102. However, it is understood that the locator assembly 100 can include additional components, systems, subsystems, and elements other than those specifically shown and/or described herein. Additionally, or alternatively, the locator assembly 100 can omit one or more of the components, systems, subsystems, and elements that are specifically shown and/or described herein. For example, in one non-exclusive alternative embodiment, the locator assembly 100 can be configured without the plurality of electrodes 102. In such alternative embodiment, the locator assembly 100 can include only the device body 112 and function simply as a stent within or near the heart 101 of the patient, or within any other vessel within the body of the patient. It is appreciated that such embodiment would not specifically include the capabilities for locating arrhythmogenic foci 732 in or near the heart 101, but would rather function as a stent for purposes of holding open whatever vessel of the body of the patient in which the locator assembly 100 is deployed. In some embodiments, components of the locator assembly 100 can be positioned in a different manner than what is specifically illustrated in FIG. 1A.

In some embodiments, the locator assembly 100 and/or the device body 112 can have the same or a somewhat similar design or structure as a bare-metal stent, as one non-limiting, non-exclusive example.

The device body 112 provides at least some structure for the locator assembly 100. In certain embodiments, as shown, the device body 112 of the locator assembly 100 provides the general overall physical structure for the locator assembly 100. The device body 112 can also provide a substrate to secure certain components of the locator assembly 100, including at least the electrodes 102.

As shown, the locator assembly 100 and/or the device body 112 has at least a longitudinal axis 100*a*, but may also have other axes. The locator assembly 100 and/or the device body 112 also has a circumference 100*c* that is measured about an outer surface 100*s* of the locator assembly 100 and/or the device body 112, such as in a direction substantially transverse to the longitudinal axis 100*a*.

The device body 112 can vary depending on the design requirements of the locator assembly 100. In some embodiments, the device body 112 can be configured differently than what is specifically illustrated in FIG. 1A. The device body 112 can be any suitable structure known in the art that allows expansion and contraction in circumference.

In various embodiments, the locator assembly 100 and/or the device body 112 can be expandable to become anchored in a desired position within a portion of the heart 101 of the patient during a diagnostic procedure. More particularly, the device body 112 can include a framework and/or a lattice structure for expansion and contraction. Thus, it is appreciated that the device body 112 can be formed from flexible and/or expandable materials. In some embodiments, when the framework in the device body 112 expands in circumference, a longitudinal length of the device body 112 does not expand. In other embodiments, when the framework in the device body 112 expands in circumference, the longitudinal length of the device body 112 can also expand.

The cross-sectional shape of the locator assembly 100 and/or the device body 112 can be any suitable shape. Non-limiting, non-exclusive examples of the cross-sectional shape of the locator assembly 100 and/or the device body 112 include circular-shaped, oval-shaped, egg-shaped, pentagonal-shaped, hexagonal-shaped, heptagonal-shaped, octagonal-shaped, decagonal-shaped, or any other suitable shape. The cross-sectional shape of the locator assembly 100 and/or the device body 112 can have any number of sides and any type of curvature.

In some embodiments, if the cross-section of the locator assembly 100 and/or the device body 112 is a perfect circle and the longitudinal axis 100*a* is perfectly centered through the end of the locator assembly 100, all positions on the circumference 100*c* are equidistant from the longitudinal axis 100*a*.

As described in detail herein, in various embodiments, the device body 112 can expand and contract as needed during deployment and extraction of the locator assembly 100 within various regions of the heart 101 and body of the patient. Stated in another manner, the device body 112 individually, and/or the locator assembly 100 as a whole, is movable between a contracted state and an expanded state. In many embodiments, as described herein, the locator assembly 100 and/or the device body 112 can have a spontaneously, self-expanding design, such that the locator assembly 100 and/or the device body 112 spontaneously move from the contracted state to the expanded state when any contracting force that is otherwise exerted onto the device body 112 is removed. For example, in some embodiments, the locator assembly 100 can be implanted, positioned and/or deployed within the heart 101 through use of a deployment catheter 524 (illustrated in FIG. 5A) including a sheath 523 (illustrated in FIG. 5A).

During the initial implanting, positioning and/or deploying of the locator assembly 100, the locator assembly 100 and/or the device body 112 is typically positioned substantially fully within the sheath 523 so that the locator assembly 100 and/or the device body 112 is maintained in the contracted state. More particularly, in various embodiments, the sheath 523 can define an inner cavity 523A (illustrated in FIG. 5A) therein, and the locator assembly 100 and/or the device body 112 can be positioned substantially fully within the inner cavity 523A of the sheath 523 as the locator assembly 100 is initially implanted, positioned and/or deployed within the heart 101.

Subsequently, when it is desired to perform the actual diagnostic procedure, the locator assembly 100 and/or the device body 112 is removed from within the inner cavity 523A of the sheath 523, such as by withdrawing or retracting the sheath 523 relative to the locator assembly 100, so that it spontaneously moves from the contracted state to the expanded state.

Then, upon completion of the diagnostic procedure, the locator assembly 100 and/or the device body 112 can be moved back into the inner cavity 523A of the sheath 523, with the locator assembly 100 and/or the device body 112 gradually moving back to the contracted state.

It is appreciated that, with the spontaneous movement of the locator assembly 100 and/or the device body 112 from the contracted state to the expanded state, the deployment catheter 524 and/or the locator assembly 100 should include a suitable means for maintaining engagement between the device body 112 and the inner cavity 523A of the sheath 523 during deployment and use of the locator assembly 100 in order that the device body 112 can then subsequently be moved back within the inner cavity 523A of the sheath 523. If the locator assembly 100 and/or the device body 112 become fully disengaged from the sheath 523 during deployment and use of the locator assembly 100, there may be no adequate means for quickly and easily moving the locator assembly 100 and/or the device body 112, when in the expanded state, back into the inner cavity 523A of the sheath 523. Thus, in various embodiments, the locator assembly 100 and/or the deployment catheter 524 can include additional features or components that are configured to ensure that the locator assembly 100 and/or the device body 112 always remains engaged with the inner cavity 523A of the sheath 523 during any use of the locator assembly 100. As utilized herein, the locator assembly 100 and/or the device body 112 remaining "engaged" with the inner cavity 523A of the sheath 523 means that there is always some type of physical connection (which can be a direct physical connection or an indirect physical connection) between the locator assembly 100 and/or the device body 112 with the inner cavity 523A of the sheath 523 during any use of the locator assembly 100.

The ability to have the locator assembly 100 and/or the device body 112 move out of and back into the inner cavity 523A of the sheath 523 and/or remain engaged with the inner cavity 523A of the sheath 523, as described, can be accomplished in any suitable manner. For example, in many embodiments, the described ability to have the locator assembly 100 and/or the device body 112 move out of and back into the sheath 523, during use and subsequent removal of the locator assembly 100 from within the heart 101 of the patient, can be accomplished, at least in part, by having control of movement of the locator assembly 100 and the sheath 523 be independent of one another. Although the locator assembly 100 and the sheath 523 are positioned within the heart 101 together, with the locator assembly 100 and/or the device body 112 positioned within the inner cavity 523A of the sheath 523, the means of controlling the movement of the locator assembly 100 and the sheath 523 can still be independent of one another. In certain embodiments, the locator assembly 100 and/or the device body 112 can be coupled to a guidewire 525 (illustrated in FIG. 5A) such that the guidewire 525 is used to guide movement of the locator assembly 100 and/or the device body 112; while movement of the sheath 523 can be guided separately and independently, such as through use of a second guidewire (not shown) or simply by more directly guiding the movement of the sheath 523, such as by having direct contact with and control of movement of the sheath 523.

Additionally, or in the alternative, in certain embodiments, the device body 112 can be tethered to the sheath 523, such as through the use of a tethering system 521 (illustrated in FIG. 5C) of any suitable design that is coupled to the device body 112 and that extends into and/or through the inner cavity 523A of the sheath 523. The tethering system 521 enables the locator assembly 100 and/or the device body 112 to be relatively quickly and easily moved back within the inner cavity 523A of the sheath 523, such as by simply moving the sheath 523 toward the locator assembly 100 in order to recapture the locator assembly 100 and/or the device body 112. Once back within the inner cavity 523A of the sheath 523 and in the contracted state, the locator assembly 100 and/or the device body 112 can be removed or retrieved from the heart 101 of the patient.

Further, or in the alternative, in some embodiments, the sheath 523 and/or the device body 112 can incorporate a removal inhibitor 626 (illustrated in FIG. 6) that inhibits the device body 112 from being fully removed from the inner cavity 523A of the sheath 523. The removal inhibitor 626 can have any suitable design for purposes of inhibiting the device body 112 from being fully removed from the inner cavity 523A of the sheath 523. It is appreciated, however, that the portion of the device body 112 that is removed from the sheath 523 will still be able to spontaneously expand from the contracted state to the expanded state in order to be effectively utilized for purposes of accurately determining a location of the arrhythmogenic foci 732 in or near the heart 101.

In certain implementations, the locator assembly 100 and/or the device body 112 can be removably implanted and/or positioned within the heart 101 for only a single diagnostic procedure for purposes of locating the arrhythmogenic foci 732 in or near the heart 101. In such implementations, when in the expanded state, the locator assembly 100 and/or the device body 112 can function as a stent to expand and/or hold open portions of the heart 101 such as valves, veins, sinuses, etc. In some implementations, due to its ability to spontaneously and/or passively move between the contracted state and the expanded state, the locator assembly 100 and/or the device body 112 can be said to include, function as and/or can be referred to as a “self-expandable stent”. Further, because the locator assembly 100 is often only positioned within the heart 101 for a relatively short period of time and/or for only a single use before being removed from the heart 101, the locator assembly 100 and/or the device body 112 can be said to be “retrievable” and/or “removable”. It is appreciated that the terms noted in this paragraph as referring to the locator assembly 100 and/or the device body 112 can be equally utilized for any embodiments of the locator assembly 100 and/or the device body 112 illustrated and described herein.

In various embodiments, the locator assembly 100 can be configured to provide cardiac telemetry monitoring and sampling of electrophysiological signals from the heart 101 of the patient, such as through use of the electrodes 102. It is appreciated that, by providing the locator assembly 100 with telemetry capabilities, the locator assembly 100 can be more suitable for patients with asymptomatic, rare, or intermittent atrial fibrillation episodes.

In certain implementations, the locator assembly 100 can sample electrocardiogram signals from the heart 101 of the patient periodically (in either even or uneven time increments) throughout a relatively short sampling period. In some embodiments, the sampling period can be less than approximately one hour in length. For example, in some non-exclusive implementations, the sampling period can be less than approximately 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes and/or 1 hour in duration. In other embodiments, the sampling period can be greater than one hour in duration. It is appreciated, however, that the locator assembly 100 can capture an arrhythmia or arrhythmogenic foci 732 that may not be captured during a shorter sampling period by providing additional extended sampling periods. [Are the noted time periods accurate for this retrievable, self-expandable stent embodiment?]

In certain embodiments, the locator assembly 100 and/or the device body 112 is positioned and expanded within the heart 101 of the patient. In some embodiments, the locator assembly 100 and/or the device body 112 can include, incorporate and/or operate somewhat similarly to an expandable stent. In various implementations, the locator assembly 100 and/or the device body 112 can be removably positioned within the patient, such as with the locator assembly 100 and/or the device body 112 being removed from within the patient following a one-time, designed usage over a designated sampling period for locating the arrhythmogenic foci 732.

In various embodiments, the locator assembly 100 can be configured for use by the patient while the patient receives a magnetic resonance imaging scan, or other imaging procedures. In other words, the locator assembly 100 can have shielding and/or resistance to varying types of external electromagnetic radiation. In some embodiments, the locator assembly 100 can be automatically activated within the heart 101 of the patient. In certain embodiments, the locator assembly 100 can be manually activated by the patient or healthcare personnel.

The electrodes 102 record and sense electrical signals (such as electrophysiological signals) sent from the heart 101 and nearby portions of the body. In some embodiments, the electrodes 102 can record the atrial activity and related electrical impulses.

The type of electrodes 102 can vary depending on the design requirements of the locator assembly 100. In some embodiments, the electrodes 102 can be positioned in different configurations than what is specifically illustrated in FIG. 1A.

The electrodes 102 can include any suitable types of electrodes, including one or more electrocardiogram electrodes (as a non-limiting, non-exclusive example). The electrodes 102, when positioned in pairs, can form bipolar electrodes. The electrodes 102 can be coupled and decoupled from the locator assembly 100 and/or the device body 112 to repair or replace defective or otherwise inoperable electrodes 102 of the locator assembly 100. The locator assembly 100 can include any suitable number of electrodes 102. In some embodiments, such as the embodiment shown in FIG. 1A, the locator assembly 100 can include 16 electrodes 102. In other embodiments, the locator assembly 100 can include 2, 4, 6, 8, 10, 12, 14, 16, 18, 20, 22, 24, 26, 28, 30, or 32 electrodes 102. In certain embodiments, the locator assembly can 100 can include greater than 32 electrodes.

The electrodes 102 can be distributed about the circumference 100*c* in a pattern, either in the longitudinal and/or circumferential directions or on any suitable portion of the locator assembly 100 and/or the device body 112. About the circumference 100*c* of the locator assembly 100 and/or the device body 112, the electrodes 102 can be spaced apart by 10, 20, 30, 45, 60, 72, 90, 120, or 180 degrees. In other embodiments, the electrodes 102 can be spaced apart by approximately 5, 15, 25, 35, 40, 50, 55, 65, 70, 75, 80, 85, 95, 100, 105, 110, 115, 125, 130, 135, 140, 145, 150, 155, 160, 165, 170 or 175 degrees, or any other suitable spacing from one another about the circumference 100*c* of the locator assembly 100 and/or the device body 112.

In some embodiments, the electrodes 102 can be distributed in a somewhat circular, oval, cylindrical, or any suitable pattern about the locator assembly 100 and/or the device body 112. In one embodiment, the electrodes 102 can be evenly spaced apart from one another along the longitudinal axis 100*a* and/or about the circumference 100*c* of the locator assembly 100. In alternative embodiments, the electrodes 102 can be spaced apart from one another along the longitudinal axis 100*a* and/or about the circumference 100*c* of the locator assembly 100 in an uneven, asymmetrical, semi-random or random manner.

The external device 105 can vary depending on the design requirements of the locator assembly 100. In particular, the external device 105 can be any suitable type of computing and/or processing device depending on the design requirements of the locator assembly 100.

The external device 105 can communicate with the locator assembly 100 to enable (i) the transfer of data between the locator assembly 100 and the external device 105, (ii) the utilization of processing capabilities of the external device 105 so that the data transferred to the external device 105 can be quickly processed to accurately locate the arrhythmogenic foci 732, and/or (iii) the storage of data on the external device 105 following the transfer of the data from the locator assembly 100 to the external device 105. In some embodiments, the external device 105 can communicate with the locator assembly 100 to execute a set of processing instructions on the locator assembly 100.

The connection between the locator assembly 100 and the external device 105 can be accomplished in any suitable manner. For example, in one embodiment, as shown in FIG. 1A, the connection between the locator assembly 100 and the external device 105 can be accomplished through the inclusion of one or more wires 107 that extend between the locator assembly 100 and the external device 105. Data collected by the locator assembly 100 can thus be sent through the wires 107 to the external device 105. Alternatively, in another embodiment, the connection between the locator assembly 100 and the external device 105 can be accomplished through the inclusion of a communicator 404 (illustrated in FIG. 4) as part of the locator assembly 100, which can be coupled to the device body 112. In particular, in such alternative embodiment, the communicator 404 is used by the locator assembly 100 for wireless communication between the locator assembly 110 and the external device 105. Data collected by the locator assembly 100 can thus be sent wirelessly via the communicator 404 to the external device 105.

Figure 1B:
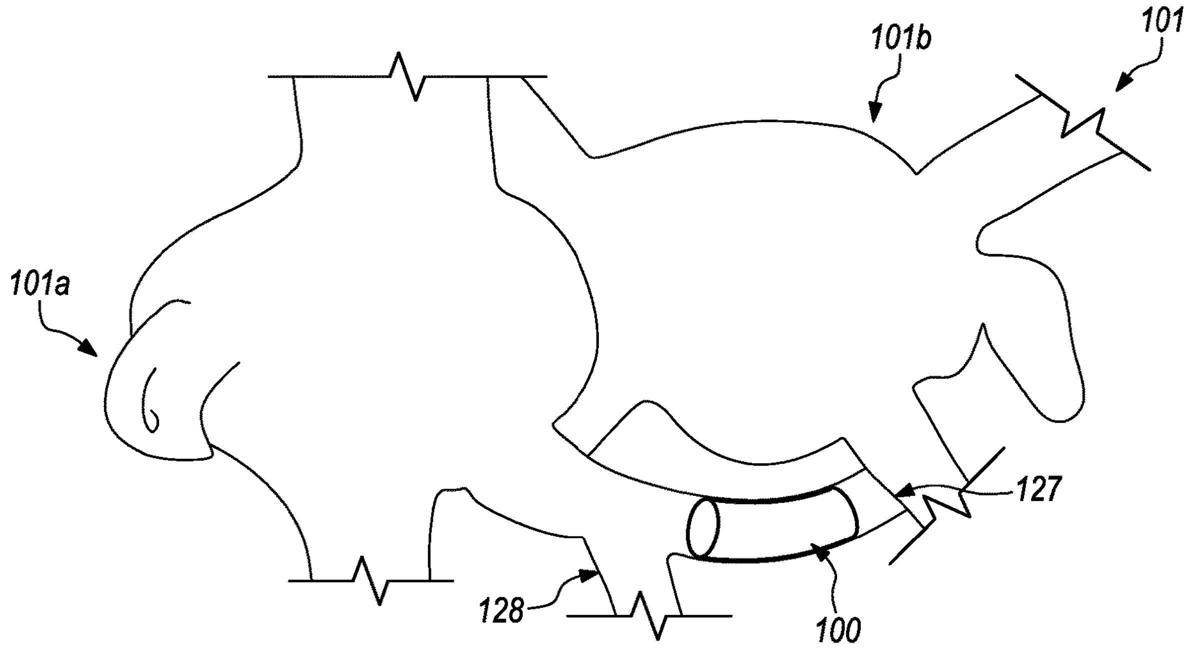
FIG. 1B is a simplified illustration of the heart and an embodiment of the locator assembly for locating the arrhythmogenic foci in or near the heart, the locator assembly being positioned within a portion of the heart.

FIG. 1B is a simplified illustration of the heart 101 and an embodiment of the locator assembly 100 positioned within the heart 101. The heart 101 includes a right atrium 101*a* and a left atrium 101*b*. As shown, the locator assembly 100 can be flexible to conform to portions of the heart 101 such as valves, veins, sinuses, etc. In particular, in the embodiment shown in FIG. 1B, the locator assembly 100 can be positioned in a coronary sinus 127 near a vena cordis media 128. However, it is understood that the locator assembly 100 can equally be positioned in other locations in or around the heart 101.

As described in detail herein below, the locator assembly 100 is typically implanted and/or positioned within the heart 101 through use of a deployment catheter 524 (illustrated in FIG. 5A) including a sheath 523 (illustrated in FIG. 5A). In various embodiments, with the locator assembly 100 often being implanted, used, and then removed from the heart 101 within a relatively short period of time, the locator assembly 100 and/or the device body 112 can be configured to remain engaged with an inner cavity 523A (illustrated in FIG. 5A) as defined within the sheath 523 throughout a diagnostic procedure. With such design, the locator assembly 100 and/or the device body 112 can be quickly and easily moved out of and back into the inner cavity 523A of the sheath 523, and subsequently quickly and easily removed from the heart 101 upon completion of the diagnostic procedure. However, it is noted that the deployment catheter 524 and the sheath 523 are not illustrated in FIG. 1B for purposes of clarity and ease of illustration.

Figure 2A:
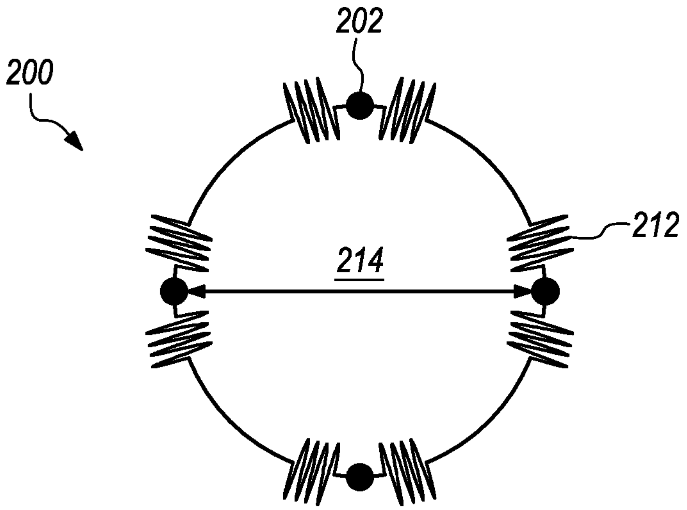
FIG. 2A is a simplified end view of an embodiment of the locator assembly, shown in a contracted state.

FIG. 2A is a simplified front elevation view of an embodiment of the locator assembly 200 being shown in the contracted state. In particular, FIG. 2A illustrates that the locator assembly 200 includes the device body 212 and the electrodes 202 that are coupled thereto, and the locator assembly 200 and/or the device body 212 is being shown in the contracted state.

As used herein, the "contracted state" is understood to mean the locator assembly 200 and/or the device body 212 is contracted or unexpanded. In the contracted state, the structures and/or components of the locator assembly 200, including the electrodes 202, can be at least partially contracted. For example, in one embodiment of the locator assembly 200 shown in FIG. 2A, the device body 212 is in the contracted state when the framework in the device body 212 is contracted or unexpanded. For ease of understanding, the contracted state of the device body 212 in FIG. 2A is exaggerated to demonstrate the flexibility and/or contraction of the device body 212.

As shown in FIG. 2A, while in the contracted state, the locator assembly 200 has a contracted diameter 214. In some embodiments, the contracted diameter 214 illustrated and described herein can be between approximately 0.01 mm and 20.00 mm. In various non-exclusive embodiments, the contracted diameter 214 can be approximately 0.01 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, 10 mm, 10.1 mm, 10.2 mm, 10.3 mm, 10.4 mm, 10.5 mm, 10.6 mm, 10.7 mm, 10.8 mm, 10.9 mm, 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.1 mm, 17.2 mm, 17.3 mm, 17.4 mm, 17.5 mm, 17.6 mm, 17.7 mm, 17.8 mm, 17.9 mm, 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, or 20 mm. In other embodiments, the contracted diameter 214 can be less than approximately 0.01 mm or greater than approximately 20.00 mm.

Figure 2B:
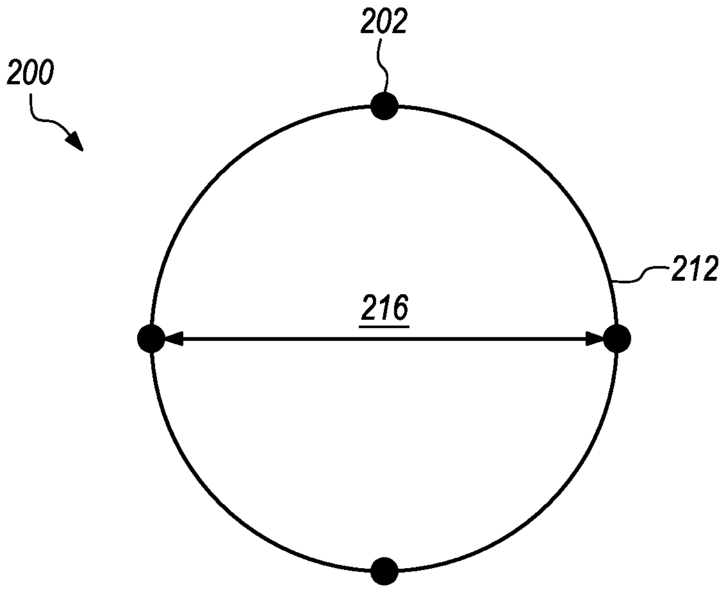
FIG. 2B is a simplified end view of an embodiment of the locator assembly, shown in an expanded state.

FIG. 2B is a simplified front elevation view of an embodiment of the locator assembly 200 being shown in the expanded state. In particular, FIG. 2B again illustrates that the locator assembly 200 includes the device body 212 and the electrodes 202 that are coupled thereto, but the locator assembly 200 has now been moved to the expanded state, such that the device body 212 has been expanded relative to the condition when the device body 212 is in the contracted state.

As used herein, the "expanded state" is understood to mean the locator assembly 200 and/or the device body 212 is expanded outwardly from the contracted state so that the locator assembly 200 and/or the device body 212 has an increased circumference and/or an increased diameter relative to the contracted state. Thus, as illustrated, the device body 212 individually and/or the locator assembly 200 as a whole is movable between the contracted state and the expanded state.

As shown in FIG. 2B, while in the expanded state, the locator assembly 200 has an expanded diameter 216 that is greater than the contracted diameter 214 (illustrated in FIG. 2A). In some embodiments, the expanded diameter 216 illustrated and described herein can be between approximately 0.01 mm and 20.00 mm. In various non-exclusive embodiments, the expanded diameter 216 can be approximately 0.01 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 3.7 mm, 3.8 mm, 3.9 mm, 4 mm, 4.1 mm, 4.2 mm, 4.3 mm, 4.4 mm, 4.5 mm, 4.6 mm, 4.7 mm, 4.8 mm, 4.9 mm, 5 mm, 5.1 mm, 5.2 mm, 5.3 mm, 5.4 mm, 5.5 mm, 5.6 mm, 5.7 mm, 5.8 mm, 5.9 mm, 6 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm, 7.9 mm, 8 mm, 8.1 mm, 8.2 mm, 8.3 mm, 8.4 mm, 8.5 mm, 8.6 mm, 8.7 mm, 8.8 mm, 8.9 mm, 9 mm, 9.1 mm, 9.2 mm, 9.3 mm, 9.4 mm, 9.5 mm, 9.6 mm, 9.7 mm, 9.8 mm, 9.9 mm, 10 mm, 10.1 mm, 10.2 mm, 10.3 mm, 10.4 mm, 10.5 mm, 10.6 mm, 10.7 mm, 10.8 mm, 10.9 mm, 11 mm, 11.1 mm, 11.2 mm, 11.3 mm, 11.4 mm, 11.5 mm, 11.6 mm, 11.7 mm, 11.8 mm, 11.9 mm, 12 mm, 12.1 mm, 12.2 mm, 12.3 mm, 12.4 mm, 12.5 mm, 12.6 mm, 12.7 mm, 12.8 mm, 12.9 mm, 13 mm, 13.1 mm, 13.2 mm, 13.3 mm, 13.4 mm, 13.5 mm, 13.6 mm, 13.7 mm, 13.8 mm, 13.9 mm, 14 mm, 14.1 mm, 14.2 mm, 14.3 mm, 14.4 mm, 14.5 mm, 14.6 mm, 14.7 mm, 14.8 mm, 14.9 mm, 15 mm, 15.1 mm, 15.2 mm, 15.3 mm, 15.4 mm, 15.5 mm, 15.6 mm, 15.7 mm, 15.8 mm, 15.9 mm, 16 mm, 16.1 mm, 16.2 mm, 16.3 mm, 16.4 mm, 16.5 mm, 16.6 mm, 16.7 mm, 16.8 mm, 16.9 mm, 17 mm, 17.1 mm, 17.2 mm, 17.3 mm, 17.4 mm, 17.5 mm, 17.6 mm, 17.7 mm, 17.8 mm, 17.9 mm, 18 mm, 18.1 mm, 18.2 mm, 18.3 mm, 18.4 mm, 18.5 mm, 18.6 mm, 18.7 mm, 18.8 mm, 18.9 mm, 19 mm, 19.1 mm, 19.2 mm, 19.3 mm, 19.4 mm, 19.5 mm, 19.6 mm, 19.7 mm, 19.8 mm, 19.9 mm, or 20 mm. In other embodiments, the expanded diameter 216 can be less than approximately 0.01 mm or greater than approximately 20.00 mm. However, although the non-exclusive examples disclosed for the expanded diameter 216 are generally the same as the non-exclusive examples for the contracted diameter 214, it is appreciated that the expanded diameter 216 will be greater than the contracted diameter 214.

In certain embodiments, a ratio of the expanded diameter 216 to the contracted diameter 214 for the locator assembly 200 herein can be greater than approximately 1:1 and less than or equal to approximately 20:1. In some such non-exclusive embodiments, the ratio of the expanded diameter 216 to the contracted diameter 214 for the locator assembly 200 can be approximately 1.01:1, 1.1:1, 1.2:1, 1.3:1, 1.4:1, 1.5:1, 1.6:1, 1.7:1, 1.8:1, 1.9:1, 2:1, 2. 1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1, 5:1, 5. 1:1, 5.2:1, 5.3:1, 5.4:1, 5.5:1, 5.6:1, 5.7:1, 5.8:1, 5.9:1, 6:1, 6.1:1, 6.2:1, 6.3:1, 6.4:1, 6.5:1, 6.6:1, 6.7:1, 6.8:1, 6.9:1, 7:1, 7.1:1, 7.2:1, 7.3:1, 7.4:1, 7.5:1, 7.6:1, 7.7:1, 7.8:1, 7.9:1, 8:1, 8.1:1, 8.2:1, 8.3:1, 8.4:1, 8.5:1, 8.6:1, 8.7:1, 8.8:1, 8.9:1, 9:1, 9.1:1, 9.2:1, 9.3:1, 9.4:1, 9.5:1, 9.6:1, 9.7:1, 9.8:1, 9.9:1, 10:1, 10.1:1, 10.2:1, 10.3:1, 10.4:1, 10.5:1, 10.6:1, 10.7:1, 10.8:1, 10.9:1, 11:1, 11.1:1, 11.2:1, 11.3:1, 11.4:1, 11.5:1, 11.6:1, 11.7:1, 11.8:1, 11.9:1, 12:1, 12.1:1, 12.2:1, 12.3:1, 12.4:1, 12.5:1, 12.6:1, 12.7:1, 12.8:1, 12.9:1, 13:1, 13.1:1, 13.2:1, 13.3:1, 13.4:1, 13.5:1, 13.6:1, 13.7:1, 13.8:1, 13.9:1, 14:1, 14.1:1, 14.2:1, 14.3:1, 14.4:1, 14.5:1, 14.6:1, 14.7:1, 14.8:1, 14.9:1, 15:1, 15.1:1, 15.2:1, 15.3:1, 15.4:1, 15.5:1, 15.6:1, 15.7:1, 15.8:1, 15.9:1, 16:1, 16.1:1, 16.2:1, 16.3:1, 16.4:1, 16.5:1, 16.6:1, 16.7:1, 16.8:1, 16.9:1, 17:1, 17.1:1, 17.2:1, 17.3:1, 17.4:1, 17.5:1, 17.6:1, 17.7:1, 17.8:1, 17.9:1, 18:1, 18.1:1, 18.2:1, 18.3:1, 18.4:1, 18.5:1, 18.6:1, 18.7:1, 18.8:1, 18.9:1, 19:1, 19.1:1, 19.2:1, 19.3:1, 19.4:1, 19.5:1, 19.6:1, 19.7:1, 19.8:1, 19.9:1, or 20:1. Alternatively, in other embodiments, the ratio of the expanded diameter 216 to the contracted diameter 214 for the locator assembly 200 can be greater than approximately 20:1, or anywhere between 1:1 and 1.01:1.

Figure 3:
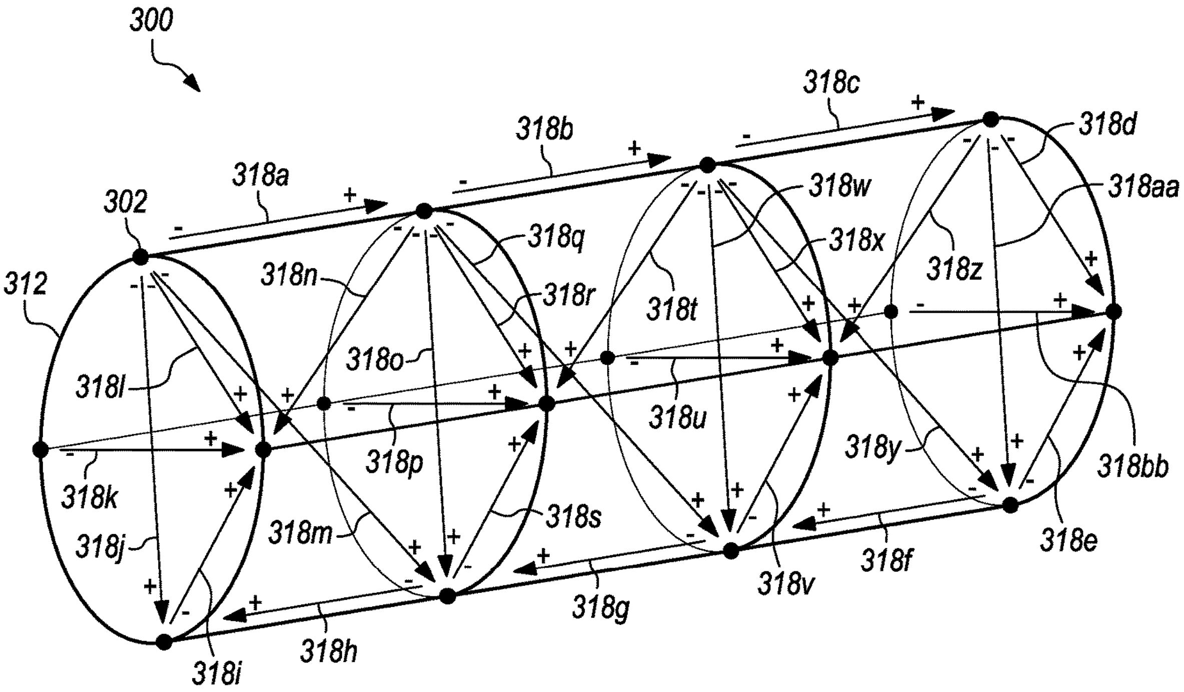
FIG. 3 is a simplified, partially transparent, perspective view of an embodiment of the locator assembly showing bipolar relationships between pairs of electrodes within the locator assembly.

FIG. 3 is a simplified, partially transparent, perspective view of an embodiment of the locator assembly 300 illustrating bipolar relationships between electrodes 302 within the locator assembly 300. In the embodiment illustrated in FIG. 3, the locator assembly 300 can include the device body 312 and a plurality of bipoles 318*a*-318*bb*. The electrodes 302 can be bipolar electrodes having a negative polarity or positive polarity. In FIG. 3, the bipoles 318*a*-318*bb* are illustrated as vectors that indicate bipoles of electrical current running across the locator assembly 300 from the electrode 302 having a negative polarity to the electrode 302 having a positive polarity. The electrode 302 having a negative polarity is sometimes referred to herein as a cathode, and the electrode 302 having a positive polarity is sometimes referred to herein as an anode.

The bipoles 318*a*-318*bb* are formed between two electrical components (such as the anode and the cathode) with opposing polarities. In the bipoles 318*a*-318*bb*, the electrical current runs across the locator assembly 300 between the electrical components of opposing polarities. The electrodes 302 can be excited by applying a current or a voltage to produce the bipoles 318*a*-318*bb* between the anode and cathode. The current or the voltage can be applied to the electrodes 302 by the locator assembly 300 and/or the external device 105 (illustrated in FIG. 1).

The bipoles 318*a*-318*bb* can vary depending on the design requirements of the locator assembly 300 and/or the electrodes 302. In some embodiments, such as illustrated in FIG. 3, a network of bipoles 318*a*-318*bb*, including a plurality of anodes and cathodes, are arranged on the locator assembly 300. Multiple bipoles 318*a*-318*bb* or multiple bipole networks can be arranged in any suitable portion of the locator assembly 300. The bipoles 318*a*-318*bb* can be distributed about the longitudinal axis 100*a* (illustrated in FIG. 1A) in a pattern, either in the longitudinal and/or circumferential directions or about or along any other suitable axis.

In some embodiments, the bipoles 318*a*-318*bb* can be distributed in a somewhat circular, oval, cylindrical, or any suitable pattern about the locator assembly 300. In one embodiment, the bipoles 318*a*-318*bb* can be evenly spaced apart from one another along the longitudinal axis 100*a* and/or about the circumference 100*c* (illustrated in FIG. 1A) of the locator assembly 300. In alternative embodiments, the bipoles 318*a*-318*bb* can be spaced apart from one another along the longitudinal axis 300*a* and/or about the circumference 100*c* of the locator assembly 300 in an uneven, semi-random, or random manner. While 28 bipoles 318*a*-318*bb* are displayed in the embodiment shown in FIG. 3, it is understood that more than 28 bipoles 318*a*-318*bb* or fewer than 28 bipoles 318*a*-318*bb* can be utilized by the locator assembly 300.

Figure 4:
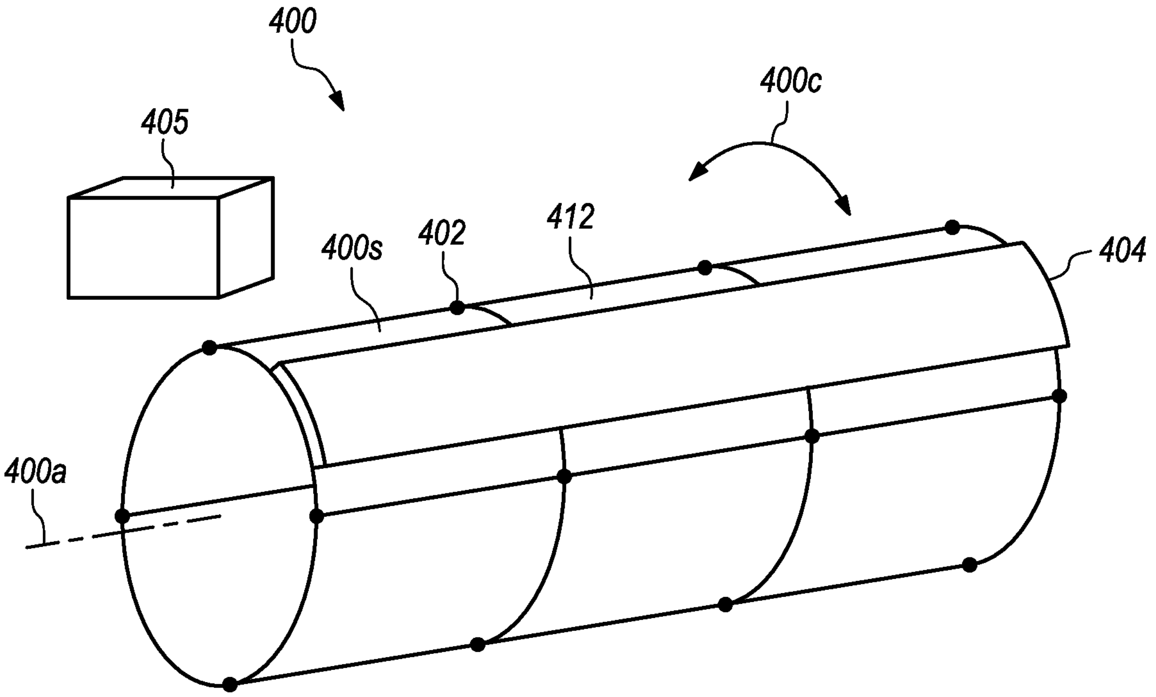
FIG. 4 is a simplified perspective view of another embodiment of the locator assembly.

FIG. 4 is a simplified perspective view of another embodiment of the locator assembly 400 that is utilized for locating arrhythmogenic foci 732 (illustrated in FIG. 7) in or near the heart 101 (illustrated in FIG. 1B), and an external device 405 that is configured to communicate with the locator assembly 400. In this embodiment, the locator assembly 400 and the external device 405 are substantially similar in design and operation to the locator assembly 100 and the external device 105 illustrated and described in detail herein above in relation to FIG. 1A. More particularly, as shown, the locator assembly 400 can again include a device body 412, and a plurality of electrodes 402 that are coupled and/or secured to the device body 412. The device body 412 and the electrodes 402 are substantially identical in terms of design and operation to what has been illustrated and described herein above. More particularly, the locator assembly 400, through use and/or operation of the device body 412 and the electrodes 402, is again configured to generate and/or collect information and data for purposes of locating the arrhythmogenic foci 732 in or near the heart 101, and then such information and data is transmitted to the external device 405 for any necessary or desired processing. Accordingly, the device body 412 and the electrodes 402 will not again be described in substantial detail with respect to the specific embodiment of the locator assembly 400 shown in FIG. 4.

As shown, similar to the previous embodiment, the locator assembly 400 and/or the device body 412 can again have at least a longitudinal axis 400*a*, and a circumference 400*c* that is measured about an outer surface 400*s* of the locator assembly 400 and/or the device body 412, such as in a direction substantially transverse to the longitudinal axis 400*a*.

With this embodiment, the locator assembly 400 is again deliverable to and/or positionable within a portion of the heart 101 of a patient for performing a diagnostic procedure of locating the arrhythmogenic foci 732 in or near the heart 101. For example, in certain implementations, the locator assembly 400 can be delivered to and/or positioned within a coronary sinus 127 (illustrated in FIG. 1B) of the heart 101 (and near a vena cordis media 128 (illustrated in FIG. 1B) of the heart 101) for purposes of locating the arrhythmogenic foci 732. Alternatively, in other implementations, the locator assembly 400 can be delivered to and/or positioned within other portions of the heart 101 for purposes of locating the arrhythmogenic foci 732. The locator assembly 400 can map precipitating episodes of clinical atrial fibrillation during the patient's daily life.

It is further noted that the locator assembly 400 and/or the device body 412 is again configured to move between a contracted state and an expanded state. In particular, the device body 412 can include a framework and/or a lattice structure for expansion and contraction such that the locator assembly 400 and/or the device body 412 can be effectively anchored in a desired position within a portion of the heart 101 of the patient during a diagnostic procedure. More specifically, as with the previous embodiments, the locator assembly 400 and/or the device body 412 can again have a spontaneously, self-expanding design, such that the locator assembly 400 and/or the device body 412 spontaneously move from the contracted state to the expanded state when any contracting force that is otherwise exerted onto the device body 412 is removed. For example, in some embodiments, the locator assembly 400 can again be implanted, positioned and/or deployed within the heart 101 through use of a deployment catheter 524 (illustrated in FIG. 5A) including a sheath 523 (illustrated in FIG. 5A).

During the initial implanting, positioning and/or deploying of the locator assembly 400, the locator assembly 400 and/or the device body 412 is again typically positioned substantially fully within an inner cavity 523A (illustrated in FIG. 5A) of the sheath 523 so that the locator assembly 400 and/or the device body 412 is maintained in the contracted state. Subsequently, when it is desired to perform the actual diagnostic procedure, the locator assembly 400 and/or the device body 412 is removed from within the inner cavity 523A of the sheath 523, such as by withdrawing or retracting the sheath 523 relative to the locator assembly 400, so that it spontaneously moves from the contracted state to the expanded state. When in the expanded state, the locator assembly 400 and/or the device body 412 can again function as a stent to expand and/or hold open portions of the heart 101 such as arteries, valves, veins, sinuses, etc. Then, upon completion of the diagnostic procedure, the locator assembly 400 and/or the device body 412 can similarly be moved back into the inner cavity 523A of the sheath 523, with the locator assembly 400 and/or the device body 412 gradually moving back to the contracted state.

As with the embodiments described above, with the spontaneous movement of the locator assembly 400 and/or the device body 412 from the contracted state to the expanded state, the deployment catheter 524 and/or the locator assembly 400 should include a suitable means for maintaining engagement between the device body 412 and the inner cavity 523A of the sheath 523 during deployment and use of the locator assembly 400 in order that the device body 412 can then subsequently be moved back within the inner cavity 523A of the sheath 523. For example, in certain embodiments, the device body 412 can again be tethered to the sheath 523, such as through the use of a tethering system 521 (illustrated in FIG. 5C) of any suitable design that is coupled to the device body 412 and that extends into and/or through the inner cavity 523A of the sheath 523. The tethering system 521 enables the locator assembly 400 and/or the device body 412 to be relatively quickly and easily moved back within the inner cavity 523A of the sheath 523, such as by simply moving the sheath 523 toward the locator assembly 400 in order to recapture the locator assembly 400 and/or the device body 412. Once back within the inner cavity 523A of the sheath 523 and in the contracted state, the locator assembly 400 and/or the device body 412 can be removed or retrieved from the heart 101 of the patient. In other embodiments, the sheath 523 and/or the device body 412 can incorporate a removal inhibitor 626 (illustrated in FIG. 6) of any suitable design that inhibits the device body 412 from being fully removed from the inner cavity 523A of the sheath 523.

As with the previous embodiments, the locator assembly 400 can again be configured to provide cardiac telemetry monitoring and sampling of electrophysiological signals from the heart 101 of the patient, such as through use of the electrodes 402. It is appreciated that, by providing the locator assembly 400 with telemetry capabilities, the locator assembly 400 can be more suitable for patients with asymptomatic, rare, or intermittent atrial fibrillation episodes. In certain implementations, the locator assembly 400 can sample electrocardiogram signals from the heart 101 of the patient periodically (in either even or uneven time increments) throughout a relatively short sampling period. In some embodiments, the sampling period can be less than approximately one hour in duration. For example, in some non-exclusive implementations, the sampling period can be less than approximately 30 seconds, 1 minute, 2 minutes, 3 minutes, 4 minutes, 5 minutes, 10 minutes, 15 minutes, 20 minutes, 25 minutes, 30 minutes, 35 minutes, 40 minutes, 45 minutes, 50 minutes, 55 minutes or 60 minutes in duration. In other embodiments, the sampling period can be greater than one hour in duration. It is appreciated, however, that the locator assembly 400 can capture an arrhythmia or arrhythmogenic foci 732 that may not be captured during a shorter sampling period by providing more extended sampling periods. [Are the noted time periods accurate for this removable, expandable stent embodiment?]

In certain implementations, the locator assembly 400 and/or the device body 412 can be removably positioned within the patient, such as with the locator assembly 400 and/or the device body 412 being removed from within the patient following a one-time, designed usage over a designated sampling period for locating the arrhythmogenic foci 732.

During any given diagnostic procedure, the electrodes 402 can again have any suitable design and be positioned in any suitable manner on or along the device body 412 in order to record and sense electrical signals (such as electrophysiological signals) sent from the heart 101 and nearby portions of the body. In some embodiments, the electrodes 402 can record the atrial activity and related electrical impulses, with such information and data being usable for purposes of locating the arrhythmogenic foci 732 in or near the heart 101. Such information and data can again be transmitted to the external device 405 for any necessary or desired processing.

However, in the embodiment illustrated in FIG. 4, the information and data is transmitted to the external device 405 in a different manner than in the previous embodiments. In particular, in this embodiment, the locator assembly 400 can further include a communicator 404, which can be coupled and/or secured to the device body 412 in any suitable manner and in any suitable position. As shown in FIG. 4, the components of the locator assembly 400, such as the electrodes 402 and the communicator 404, can be radially spaced apart from one another about the circumference 400*c*. In certain embodiments, the locator assembly 400 can include one or more platforms configured to retain corresponding components of the locator assembly 400 about the circumference 400*c*. In other embodiments, such as shown in FIG. 4, certain components of the locator assembly 400 can integrate platforms configured to enable coupling to the device body 412 of the locator assembly 400.

In certain embodiments, the communicator 404 is used by the locator assembly 400 for wireless communication between the locator assembly 400 and the external device 405 (such as any suitable computing device or processing device). Data collected by the locator assembly 400 can be sent wirelessly via the communicator 404 to the external device 405. In other words, the communicator 404 is configured to allow and/or enable communication between the locator assembly 400 and the external device 405.

The external device 405 can communicate with the locator assembly 400 to enable (i) the transfer of data between the locator assembly 400 and the external device 405, (ii) the utilization of processing capabilities of the external device 405 so that the data transferred to the external device 405 can be quickly processed to accurately locate the arrhythmogenic foci 732, and/or (iii) the storage of data on the external device 405 following the transfer of the data from the locator assembly 400 to the external device 405. In some embodiments, the external device 405 can communicate with the locator assembly 400 to execute a set of processing instructions on the locator assembly 400.

The type of communicator 404 and/or the positioning of the communicator 404 can vary depending on the design requirements of the locator assembly 400. The communicator 404 can include any suitable wireless communications device, such as a radio frequency, Bluetooth®, low energy antenna, and/or any suitable antenna as non-limiting, non-exclusive examples. The communicator 404 can also include any suitable wired communication device, such as wire antennas, dipole antennas, monopole antennas, loop antennas, transmission line antennas, etc. In some embodiments, the communicator 404 can be positioned differently than what is specifically illustrated in FIG. 4.

In various embodiments, as described herein, the locator assembly and/or the device body remain engaged with the inner cavity of the sheath during deployment, use and subsequent retrieval of the locator assembly from within the body of the patient. It is appreciated that the locator assembly and/or the deployment catheter can include any suitable features or components that are configured to ensure that the locator assembly and/or the device body always remains engaged with the inner cavity of the sheath during any use of the locator assembly. FIGS. 5A-5C and FIG. 6 are used to illustrate and describe certain alternative embodiments of the locator assembly and/or the deployment catheter that are so configured.

Figure 5A:
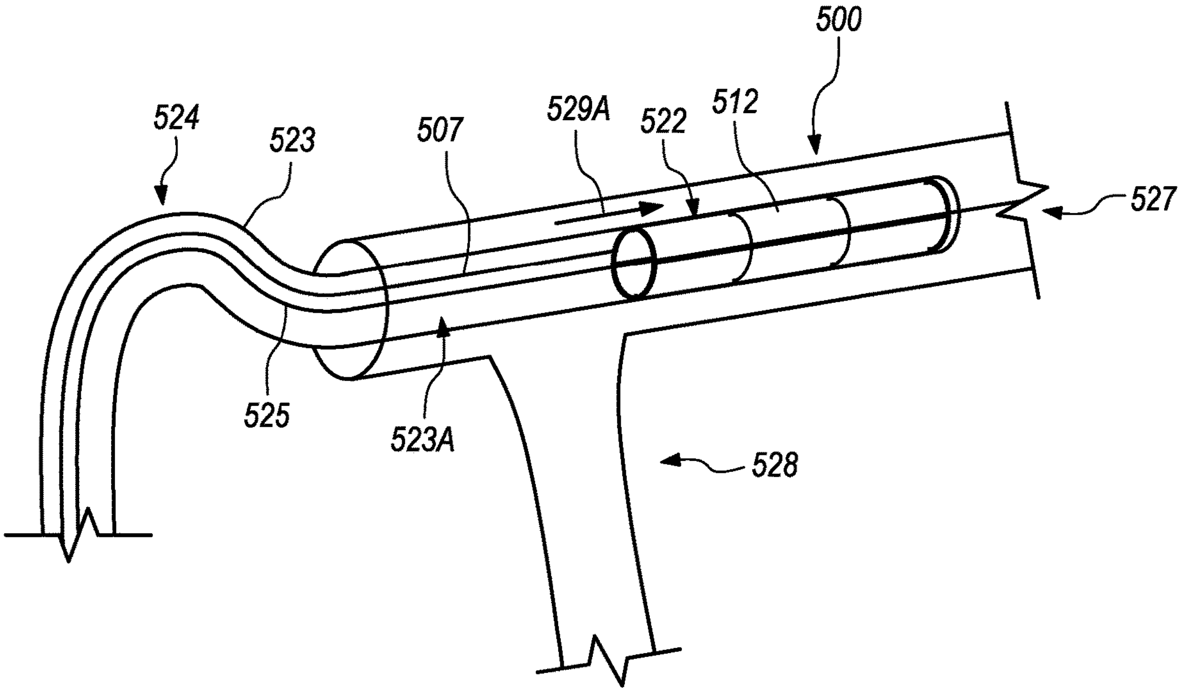
FIG. 5A is a simplified, partially transparent view of a portion of the heart, another embodiment of the locator assembly, and an embodiment of a deployment catheter, the locator assembly being shown in an initial deployment position.

FIG. 5A is a simplified, partially transparent view of another embodiment of the locator assembly 500 including a device body 512, and an embodiment of a deployment catheter 524 that includes a sheath 523, which defines an inner cavity 523A therein, and a guidewire 525. In this embodiment, the locator assembly 500 and/or the device body 512 can again include and/or incorporate a spontaneous, self-expanding design, such that the locator assembly 500 and/or the device body 512 spontaneously move from a contracted state to an expanded state when any contracting force that is otherwise exerted onto the device body 512 is removed.

In FIG. 5A, the locator assembly 500 is shown in an initial deployment position. As illustrated in FIG. 5A, the locator assembly 500 has been initially deployed, such as through use of the deployment catheter 524, and is positioned within the coronary sinus 527 of the heart 101 (illustrated in FIG. 1) near the vena cordis media 528.

As utilized herein, the locator assembly 500 and the deployment catheter 524 can be referred to collectively as a locator system 522.

The deployment catheter 524 deploys the locator assembly 500 in a portion of the heart 101. More particularly, the deployment catheter 524 initially deploys the locator assembly 500 in a deployment direction 529A (illustrated with an arrow) so that the locator assembly 500 is positioned at a desired location or target site within the heart 101, such as within the coronary sinus 527 and near the vena cordis media 528. As shown in FIG. 5A, with the locator assembly 500 in the initial deployment position, the locator assembly 500 will typically be positioned substantially fully within the inner cavity 523A of the sheath 523 of the deployment catheter 524 during such initial deployment of the locator assembly 500. When so positioned fully within the inner cavity 523A of the sheath 523, the locator assembly 500 and/or the device body 512 will be in the contracted state, as the structure of the sheath 523 will inhibit the locator assembly 500 and/or the device body 512 from moving toward the expanded state.

In some embodiments, the sheath 523 can have a substantially tubular or annular shape that defines the inner cavity 523A so that the locator assembly 500 and/or the device body 512 can be effectively maintained in the contracted state when the locator assembly 500 and/or the device body 512 is positioned therein. Alternatively, the sheath 523 can have another suitable shape that is still configured to effectively maintain the locator assembly 500 and/or the device body 512 in the contracted state when the locator assembly 500 and/or the device body 512 is positioned therein.

In various implementations, the deployment catheter 524 can deploy the locator assembly 500 in the same or similar manner as the deployment catheter 524 would deploy an expandable stent. As noted above, in some embodiments, the locator assembly 500 and/or the device body 512 can incorporate and/or include such an expandable stent within its overall structure.

The deployment catheter 524 can advance the locator assembly 500 to a target site within the coronary sinus 527. In some embodiments (such as the embodiment shown in FIG. 5A), the target site can be near a junction between the coronary sinus 527 and the vena cordis media 528. However, the target site illustrated in FIG. 5A is merely demonstrative, and it is appreciated that the locator assembly 500 can be deployed in any suitable position within the patient. The deployment catheter 524 can deploy the locator assembly 500 while the device is in the contracted state, the expanded state, or between states (in FIG. 5A, the locator assembly 500 is shown in the contracted state). It is appreciated, however, that the initial deployment will most often occur with the locator assembly 500 in the contracted state, as that would make for the easiest navigation through the structures of the heart 101 or other locations within the body of the patient.

The deployment catheter 524 can vary depending on the design requirements of the locator assembly 500. In various embodiments, as shown, the deployment catheter 524 includes the sheath 523 that defines the inner cavity 523A and provides structural protection for the locator assembly 500 as the locator assembly 500 is initially deployed within the heart 101. As noted, the size and shape of the sheath 523 are also designed to effectively maintain the locator assembly 500 in or toward the contracted state, as the positioning of the locator assembly 500 within the sheath 523 provides a physical and/or structural barrier that inhibits the self-expanding locator assembly 500 from self-expanding fully toward the expanded state. It is understood that the deployment catheter 524 can include additional components, systems, subsystems, and elements other than those specifically shown and/or described herein. Additionally, or alternatively, the deployment catheter 524 can omit one or more of the components, systems, subsystems, and elements that are specifically shown and/or described herein. In particular, the deployment catheter 524 in FIG. 5A has been simplified, and some elements of the deployment catheter 524 have been omitted for ease of understanding. In some embodiments, the deployment catheter 524 can be positioned differently than what is specifically illustrated in FIG. 5A.

In various implementations, the locator assembly 500 can be configured for a single, one-time, designed usage over a designated sampling period for locating the arrhythmogenic foci 732 (illustrated in FIG. 7) during a deployment, such that the locator assembly 500 is retrieved or removed from the patient after each procedure (and after each deployment). In this embodiment, in order to ease the ultimate retrieval or removal of the locator assembly 500 from within the body of the patient, the locator assembly 500 and/or the device body 512 remains engaged with the inner cavity 523A of the sheath 523 during full use of the locator assembly 500. More particularly, in this embodiment, the locator assembly 500 and/or the device body 512 is tethered to the sheath 523 (such as into the inner cavity 523A of the sheath 523) via the tethering system 521 (illustrated in FIG. 5C) (i) during initial implanting of the locator assembly 500 within the patient, (ii) during actual usage of the locator assembly 500 to locate the arrhythmogenic foci 732, and (iii) during subsequent removal of the locator assembly 500 from within the patient. Stated in another manner, although the locator assembly 500 is movable relative to the sheath 523, so as to allow the locator assembly 500 and/or the device body 512 to spontaneously self-expand as the locator assembly 500 and/or the device body 512 moves outside the sheath 523, the locator assembly 500 and/or the device body 512 still remains tethered to the sheath 523. As such, the locator assembly 500 and/or the device body 512 can be moved out from within the sheath 523 so that the locator assembly 500 can effectively locate the arrhythmogenic foci 732, and then can be quickly and easily moved back within the sheath 523 for ultimate retrieval or removal from within the body of the patient.

It is appreciated that the locator assembly 500 and/or the device body 512 can be tethered to the sheath 523 via the tethering system 521 in any suitable manner, (i) as the locator assembly 500 is initially deployed within or near the heart 101, (ii) as the sheath 523 is moved relative to the locator assembly 500 so that the locator assembly 500 and/or the device body 512 spontaneously moves from the contracted state to the expanded state when the locator assembly 500 is no longer restricted by being positioned within the inner cavity 523A of the sheath 523, (iii) when the locator assembly 500 is being used during a diagnostic procedure to collect information and data for purposes of locating the arrhythmogenic foci 732 within or near the heart 101, (iv) as the sheath 523 is moved relative to the locator assembly 500 so that the locator assembly 500 and/or the device body 512 moves back within the inner cavity 523A of the sheath 523 and the locator assembly 500 and/or the device body 512 moves from the expanded state back to the contracted state, and (v) when the sheath 523, with the locator assembly 500 positioned therein, is removed or retrieved from within or near the heart 101. Certain non-exclusive embodiments of the tethering system 521 will be described in greater detail herein below in relation to FIG. 5C.

In some embodiments, the deployment catheter 524 can be a percutaneous transcatheter or any suitable catheter. As shown, the deployment catheter 524 can further include the guidewire 525. The deployment catheter 524 and/or the sheath 523 can be configured to move over the guidewire 525. During initial deployment, the locator assembly 500 can be positioned substantially fully within the inner cavity 23A of the sheath 523 until the target site is reached. Subsequently, as described in greater detail herein below, when it is desired to perform an actual monitoring procedure, the sheath 523 is retracted relative to the locator assembly 500 such that the locator assembly 500 and/or the device body 512 move outside of the inner cavity 523A of the sheath 523, and can gradually and spontaneously expand toward the expanded state and be anchored in position at the target site.

The guidewire 525 can advance components (such as the locator assembly 500) through an opening of the deployment catheter 524 and/or the sheath 523. The guidewire 525 can be advanced simultaneously with the deployment catheter 524 and/or the sheath 523 within the body of the patient. The guidewire 525 can vary depending on the design requirements of the locator assembly 500 and/or the deployment catheter 524. In some embodiments, the guidewire 525 can be positioned differently than what is specifically illustrated in FIG. 5A.

As noted above, in this embodiment, the locator assembly 500 has a spontaneous, self-expanding design such that the locator assembly 500 and/or the device body 512 spontaneously moves from the contracted state to the expanded state when not otherwise restrained, such as when the locator assembly 500 is maintained in the contracted state due to its position within the inner cavity 523A of the sheath 523 of the deployment catheter 524. More specifically, as shown in FIG. 5A, the locator assembly 500 is advanced to a desired location or target site, such as into the coronary sinus 527 or other location within the body of the patient, via the delivering, pre-formed sheath 523, with the locator assembly 500 positioned therewithin. Subsequently, as described in greater detail herein below, upon retraction of the sheath 523, the locator assembly 500, and the stent structure of the device body 512 included therein, moves out of the inner cavity 523A and deploys spontaneously at the target site according to its memory properties. The locator assembly 500 then stays steady in position during the designated procedure at the target site. Thus, this embodiment provides the possibility for a passive assembly delivery option for the single, one-time, designed usage of the locator assembly 500 per deployment.

FIG. 5A also illustrates the wires 507 that can be used to transmit information and data from the locator assembly 500 to the external device 105 (illustrated in FIG. 1A).

Figure 5B:
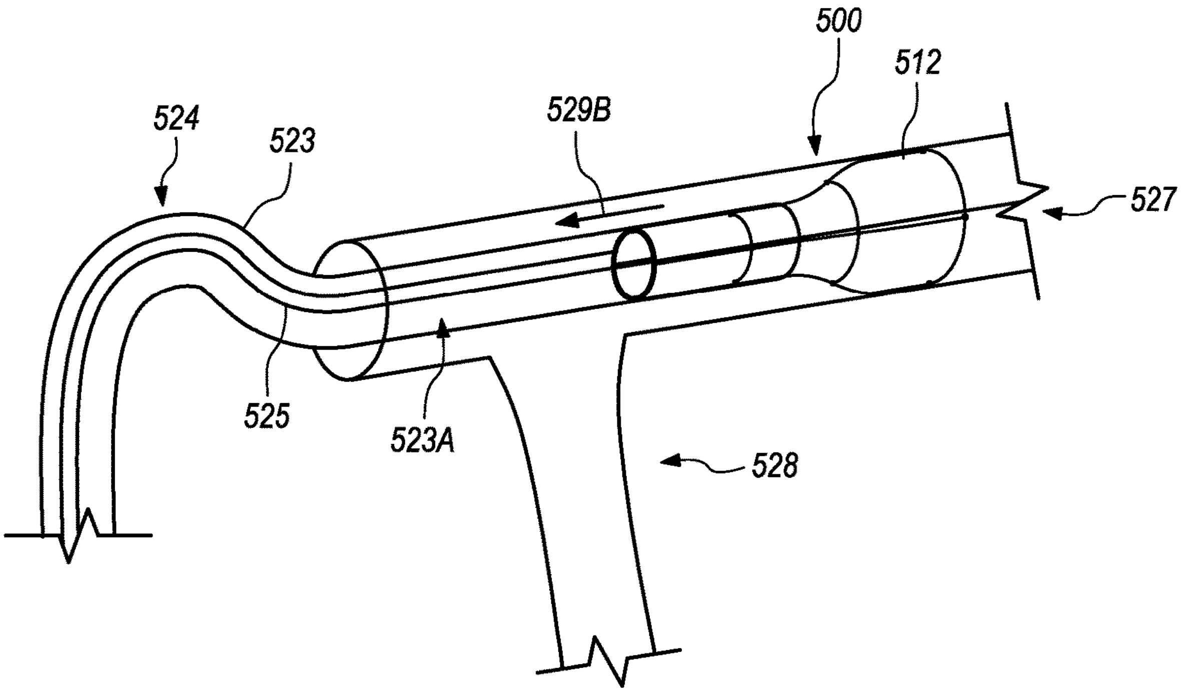
FIG. 5B is a simplified, partially transparent view of the portion of the heart, the locator assembly, and the deployment catheter illustrated in FIG. 5A, the locator assembly being shown in a partially deployed position.

FIG. 5B is a simplified, partially transparent view of the locator assembly 500 and the deployment catheter 524 illustrated in FIG. 5A, the locator assembly 500 now being shown in a partially deployed position. As shown in FIG. 5B, the locator assembly 500 is again positioned within the coronary sinus 527 of the heart 101 (illustrated in FIG. 1) and near the vena cordis media 528.

As illustrated in FIG. 5B, the sheath 523 of the deployment catheter 524 has been partially retracted in a sheath retraction direction 529B (illustrated with an arrow) so that approximately half of the locator assembly 500 is still positioned within the inner cavity 523A of the sheath 523, while the other half of the locator assembly 500 is now positioned outside of the inner cavity 523A of the sheath 523. This is considered as the partially deployed position. However, it is appreciated that the partially deployed position can include any deployment situation for the locator assembly 500 when the locator assembly 500 is at or near the target site, and is partially positioned within the inner cavity 523A of the sheath 523 and partially positioned outside the inner cavity 523A of the sheath 523.

As shown, as the structure of the locator assembly 500 and/or the device body 512 moves out from within the constraints of and/or is removed from the inner cavity 523A of the sheath 523 (such as when the sheath 523 is retracted relative to the locator assembly 500), the locator assembly 500 and/or the device body 512 spontaneously moves from the contracted state toward the expanded state. In particular, FIG. 5B illustrates that the portion of the locator assembly 500 and/or the device body 512 that is no longer positioned within and/or has been removed from the inner cavity 523A of the sheath 523 has moved from the contracted state toward the expanded state, while the other portion of the locator assembly 500 and/or the device body 512 that is still positioned within the inner cavity 523A of the sheath 523 is still maintained in the contracted state.

Figure 5C:
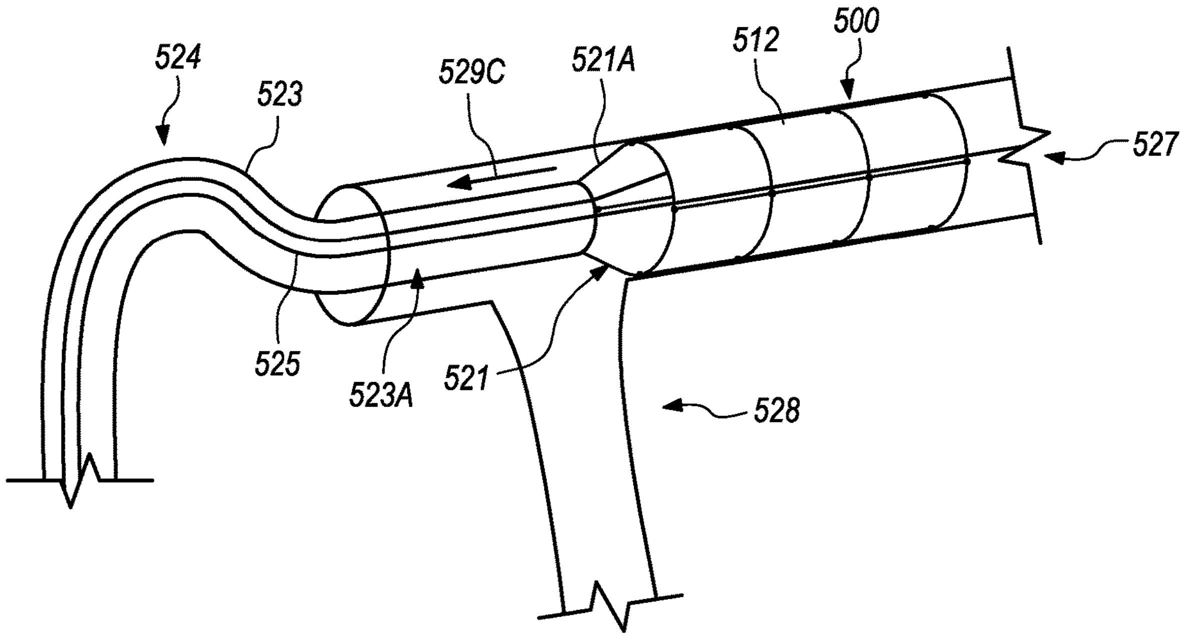
FIG. 5C is a simplified, partially transparent view of the portion of the heart, the locator assembly, and the deployment catheter illustrated in FIG. 5A, the locator assembly being shown in a fully deployed position.

FIG. 5C is a simplified, partially transparent view of the locator assembly 500 and the deployment catheter 524 illustrated in FIG. 5A, the locator assembly 500 now being shown in a fully deployed position. As shown in FIG. 5C, the locator assembly 500 is again positioned within the coronary sinus 527 of the heart 101 (illustrated in FIG. 1) and near the vena cordis media 528. In particular, the locator assembly 500 and/or the device body 512 is now positioned fully expanded at the desired location or target site and is ready to perform its designated procedure for locating the arrhythmogenic foci 732 (illustrated in FIG. 7).

As illustrated in FIG. 5C, the sheath 523 of the deployment catheter 524 has been fully retracted relative to the locator assembly 500 and/or the device body 512 in the sheath retraction direction 529C (illustrated with an arrow) so a substantial entirety of the locator assembly 500 and/or the device body 512 is now positioned outside the inner cavity 523A of the sheath 523. In this particular embodiment, this is considered as the fully deployed position.

As shown, the locator assembly 500 and/or the device body 512 has been fully removed from the inner cavity 523A of the sheath 523 so that the locator assembly 500 and/or the device body 512 is now positioned fully outside the inner cavity 523A of the sheath 523. With the locator assembly 500 and/or the device body 512 now positioned fully outside the inner cavity 523A of the sheath 523, the spontaneous self-expanding design of the locator assembly 500 and/or the device body 512 has resulted in the locator assembly 500 and/or the device body 512 moving fully from the contracted state to the expanded state.

However, as noted above, the locator assembly 500 and/or the device body 512 is still engaged with and tethered to the sheath 523 via the tethering system 521, even though the locator assembly 500 and/or the device body 512 is essentially positioned fully outside the sheath 523. With such design, upon completion of the designated procedure for locating the arrhythmogenic foci 732, the sheath 523 can again be moved in the deployment direction 529A (illustrated in FIG. 5A), and relative to the locator assembly 500, so that the locator assembly 500 and/or the device body 512 gradually moves back into the inner cavity 523A of the sheath 523. As the locator assembly 500 and/or the device body 512 moves back into the inner cavity 523A of the sheath 523, the locator assembly 500 and/or the device body

512 will move back toward the contracted state. Subsequently, once the locator assembly 500 and/or the device body 512 has moved fully back into the inner cavity 523A of the sheath 523, and the locator assembly 500 and/or the device body 512 is now fully in the contracted state, the deployment catheter 524 can be used to retrieve or remove the locator assembly 500 from within the body of the patient.

The tethering system 521 can have any suitable design for purposes of maintaining the locator assembly 500 and/or the device body 512 tethered to and engaged with the sheath 523 (such as the inner cavity 523A of the sheath 523) during deployment and usage of the locator assembly 500 within the body of the patient. For example, in certain embodiments, the tethering system 521 can include one or more tethering wires 521A that are coupled to the device body 512 and that extend into and/or through the inner cavity 523A of the sheath 523. Thus, as the sheath 523 is moved in either direction relative to the locator assembly 500 and/or the device body 512, the tethering wires 521 are still always coupled to the device body 512 and still always extend into and/or through the inner cavity 523A of the sheath 523.

It is appreciated that the tethering system 521 can include any suitable number of tethering wires 521A. It is further appreciated that the tethering wires 521A can include any suitable degree of flexibility for best enabling movement of the locator assembly 500 and/or the device body 512 into and out of the inner cavity 523A of the sheath 523.

Alternatively, the tethering system 521 can have another suitable design. For example, in certain non-exclusive alternative embodiments, the tethering wires 521A can be replaced with other suitable tethering devices, such as cords, chains, straps, belts, etc., for purposes of maintaining the locator assembly 500 and/or the device body 512 tethered to the sheath 523 during deployment and usage of the locator assembly 500 within the body of the patient.

Figure 6:
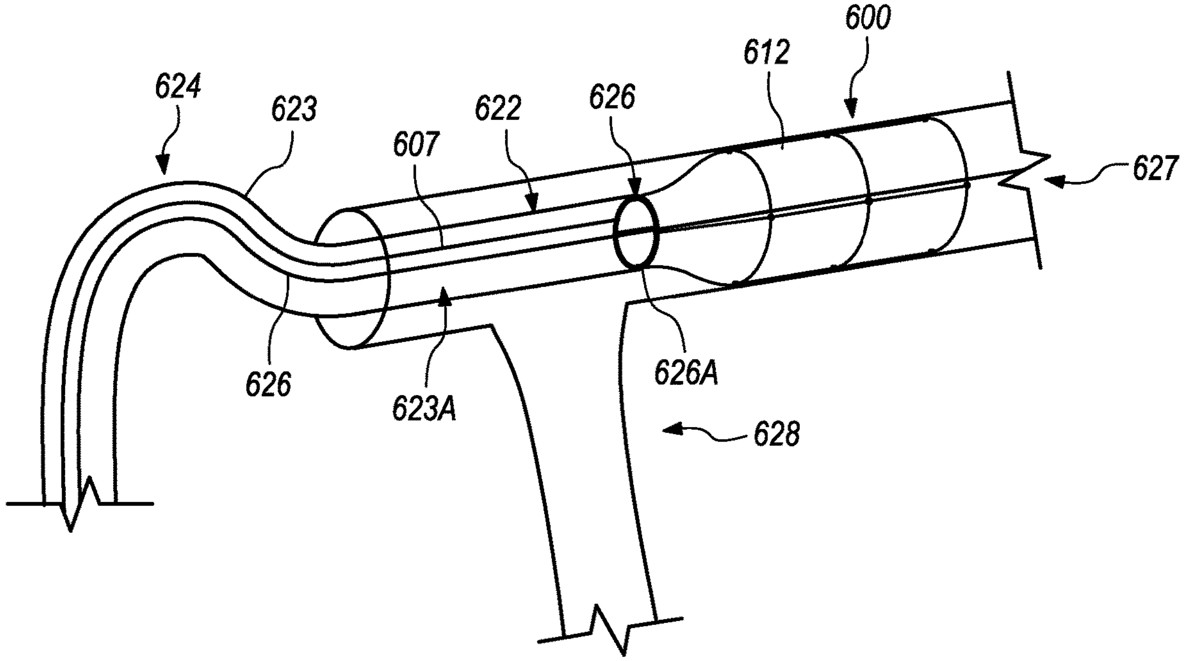
FIG. 6 is a simplified, partially transparent view of a portion of the heart, yet another embodiment of the locator assembly, and another embodiment of the deployment catheter, the locator assembly again being shown in a fully deployed position.

FIG. 6 is a simplified, partially transparent view of a yet another embodiment of the locator assembly 600 including a device body 612, and another embodiment of the deployment catheter 624 that includes a sheath 623, which defines an inner cavity 623A therein, and a guidewire 625. In this embodiment, the locator assembly 600 and/or the device body 612 can again include and/or incorporate a spontaneous, self-expanding design, such that the locator assembly 600 and/or the device body 612 spontaneously move from a contracted state to an expanded state when any contracting force that is otherwise exerted onto the device body 612 is removed.

In FIG. 6, the locator assembly 600 is again shown in a fully deployed position, with the locator assembly 600 having been deployed through use of the deployment catheter 624. As shown, the locator assembly 600 is again positioned within the coronary sinus 627 of the heart 101 (illustrated in FIG. 1) near the vena cordis media 628.

As utilized herein, the locator assembly 600 and the deployment catheter 624 can be referred to collectively as a locator system 622.

Similar to the previous embodiments, the deployment catheter 624 has been used to deploy the locator assembly 600 so that the locator assembly 600 is positioned at a desired location or target site within the heart 101, such as within the coronary sinus 627 and near the vena cordis media 628. During the initial deployment, the locator assembly 600 would again have been positioned substantially fully within the inner cavity 623A of the sheath 623 such that the locator assembly 600 and/or the device body 612 would be in the contracted state, as the structure of the sheath 623 inhibits the locator assembly 600 and/or the device body 612 from moving toward the expanded state. The general design and function of the deployment catheter 624 is substantially similar to what has been illustrated and described herein above. Accordingly, the deployment catheter 624 will not be described again in complete detail.

The guidewire 625 can advance components (such as the locator assembly 600) through an opening of the deployment catheter 624 and/or the sheath 623. The guidewire 625 can be advanced simultaneously with the deployment catheter 624 and/or the sheath 623 within the body of the patient. The guidewire 625 can vary depending on the design requirements of the locator assembly 600 and/or the deployment catheter 624. In some embodiments, the guidewire 625 can be positioned differently than what is specifically illustrated in FIG. 6.

In various implementations, the locator assembly 600 can again be configured for a single, one-time, designed usage over a designated sampling period for locating the arrhythmogenic foci 732 (illustrated in FIG. 7) during a deployment, such that the locator assembly 600 is retrieved or removed from the patient after each procedure (and after each deployment). In this embodiment, in order to ease the ultimate retrieval or removal of the locator assembly 600 from within the body of the patient, the locator assembly 600 and/or the device body 612 again is configured to remain engaged with the inner cavity 623A of the sheath 623 during full use of the locator assembly 600. However, it is appreciated that the means for maintaining the engagement between the device body 612 and the inner cavity 623A of the sheath 623 during full use of the locator assembly 600 is different than in the previous embodiments. More particularly, in this embodiment, the device body 612 and/or the sheath 623 incorporate a removal inhibitor 626 that is configured to inhibit the device body 612 from being fully removed from the inner cavity 623A of the sheath 623. The removal inhibitor 626 can have any suitable design for purposes of inhibiting the device body 612 from being fully removed from the inner cavity 623A of the sheath 623 (i) as the locator assembly 600 is initially deployed within or near the heart 101, (ii) as the sheath 623 is moved relative to the locator assembly 600 so that a portion of the locator assembly 600 and/or the device body 612 spontaneously moves from the contracted state to the expanded state when that portion of the locator assembly 600 is no longer restricted by being positioned within the inner cavity 623A of the sheath 623, (iii) when the locator assembly 600 is being used during a diagnostic procedure to collect information and data for purposes of locating the arrhythmogenic foci 732 within or near the heart 101, (iv) as the sheath 623 is moved relative to the locator assembly 600 so that the portion of the locator assembly 600 and/or the device body 612 moves back within the inner cavity 623A of the sheath 623 and the portion of the locator assembly 600 and/or the device body 612 moves from the expanded state back to the contracted state, and (v) when the sheath 623, with the locator assembly 600 again positioned fully therein, is removed or retrieved from within or near the heart 101.

For example, in certain embodiments, the removal inhibitor 626 can be provided in the form of one or more disengagement barriers 626A that can be coupled to the device body 612 of the locator assembly 600 near a proximal end of the device body 612, and/or can be coupled to the sheath 623 within the inner cavity 623A and near a distal end of the sheath 623. As shown, the disengagement barriers 626A provide a structural barrier of any suitable design that effectively inhibits the locator assembly 600 and/or the device body 612 from being fully removed from within the inner cavity 623A of the sheath 623. Alternatively, the removal inhibitor 626 can have another suitable design for inhibiting the device body 612 from being fully removed from the inner cavity 623A of the sheath 623.

It is appreciated that, in this embodiment, although the device body 612 is not fully removed from within the inner cavity 623A of the sheath 623, the portion of the device body 612 that does move outside the confines of the inner cavity 623A of the sheath 623 does effectively move from the contracted state toward the expanded state, while the portion of the device body 612 that remains within the inner cavity 623A of the sheath 623 remains in the contracted state. Thus, the locator assembly 600 an/or the device body 612 again remains engaged with the inner cavity 623A of the sheath 623 during full deployment and use of the locator assembly 600; and the locator assembly 600 and/or the device body 612 can again be quickly and easily moved back fully into the inner cavity 623A of the sheath 623, such as by moving the sheath 623 relative to the device body 612. With the locator assembly 600 and/or the device body 612 again positioned fully within the inner cavity 623A of the sheath 623, and with the locator assembly 600 and/or the device body 612 again being in the contracted state, the locator assembly 600 can easily be removed from within the body of the patient through use of the deployment catheter 624.

FIG. 6 also illustrates the wires 607 that can be used to transmit information and data from the locator assembly 600 to the external device 105 (illustrated in FIG. 1A).

Figure 7:
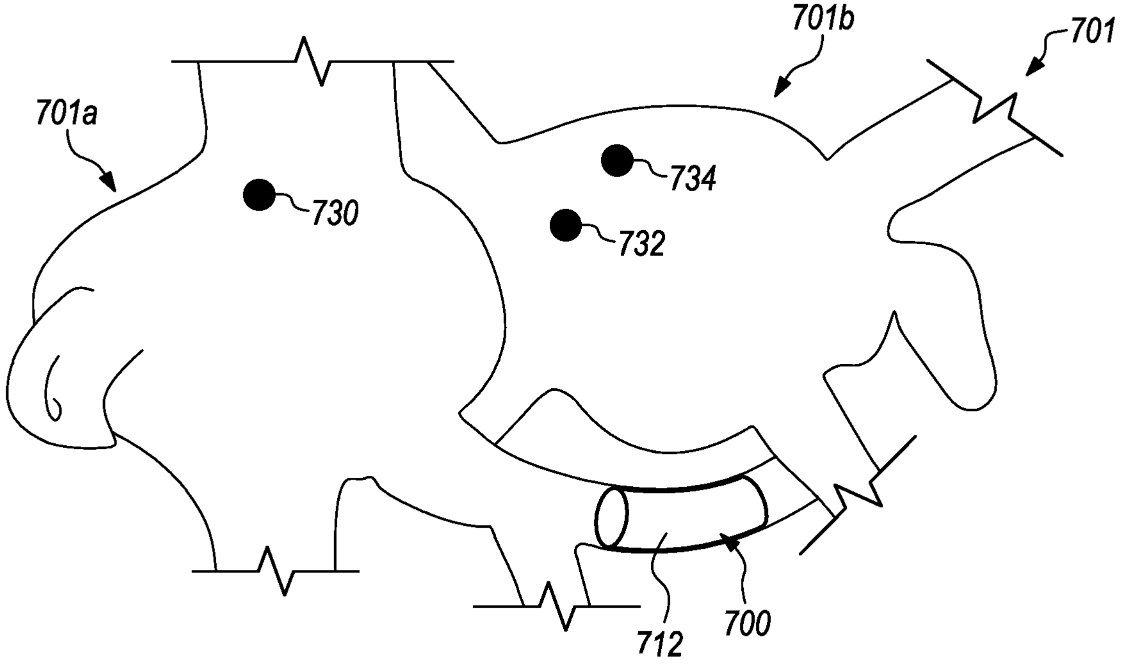
FIG. 7 is a simplified illustration of an embodiment of the locator assembly positioned within a portion of the heart, including a sinus rhythm foci, the arrhythmogenic foci, and a predicted foci in the heart.

FIG. 7 is a simplified illustration of the heart 701, including the right atrium 701*a* and the left atrium 701*b*, and an embodiment of the locator assembly 700 for determining the location of the arrhythmogenic foci 732 in or near the heart 701. It is appreciated that the locator assembly 700 shown in FIG. 7 can be in the form of the embodiment of the locator assembly 500 illustrated and described in relation to FIGS. 5A-5C and/or in the form of the embodiment of the locator assembly 600 illustrated and described in relation to FIG. 6. Alternatively, it is further appreciated that the locator assembly 700 shown in FIG. 7 can be in the form of another suitable embodiment of the locator assembly.

In FIG. 7, the locator assembly 700 is positioned within a portion of the heart 701. For ease in understanding, FIG. 7 displays exemplar locations of sinus rhythm foci 730, the arrhythmogenic foci 732, and predicted foci 734 in the heart 701.

The sinus rhythm foci 730 is the focal point of a normal sinus rhythm of the patient. In particular, in some embodiments, the sinus rhythm foci 730 represents the origin of the electrical activation sequences of the normal sinus rhythm, such as from the sino-atrial node.

The arrhythmogenic foci 732 illustrated in FIG. 7 is representative of one actual location of the focal point of an arrhythmia of the patient. It is appreciated that the arrhythmogenic foci 732 shown in FIG. 7 is merely demonstrative and/or representative, and can be located anywhere in and/or near the heart 701.

The predicted foci 734 in FIG. 7 represents the location of an artificial stimulation to determine and/or confirm whether the predicted foci 734 is the same or different than the actual arrhythmogenic foci 732. The predicted foci 734 and the arrhythmogenic foci 732 can be located at the same location (in a "matched state") or different locations (in an "unmatched state").

The artificial stimulation can be generated using any suitable device known in the art, including ablation catheters, electrical stimulation and/or pacemakers, as non-exclusive examples. The artificial stimulation device can stimulate any suitable number of predicted foci 734 during one operation and/or insertion of the artificial stimulation device into the patient. In other words, the artificial stimulation device can test various predicted foci 734 locations in rapid succession.

As described in detail herein, the locator assembly 700 is typically implanted and/or positioned within the heart 701, such as through use of the deployment catheter 524 (illustrated, for example, in FIG. 5A) and/or the deployment catheter 624 (illustrated in FIG. 6). In various embodiments, with the locator assembly 700 often being implanted, used, and then removed from the heart 701 within a relatively short period of time, the locator assembly 700 and/or the device body 712 remain engaged with the deployment catheter 524, 624, such as being engaged with the inner cavity 523A (illustrated in FIG. 5A) of the sheath 523 (illustrated in FIG. 5A) of the deployment catheter 524, and/or the inner cavity 623A (illustrated in FIG. 6) of the sheath 623 (illustrated in FIG. 6) of the deployment catheter 624, throughout the noted procedure. With such design, the locator assembly 700 can then be quickly and easily removed from the heart 701 upon completion of the procedure. However, it is noted that the deployment catheter and the sheath are not illustrated in FIG. 7 for purposes of clarity and ease of illustration.

Figure 8:
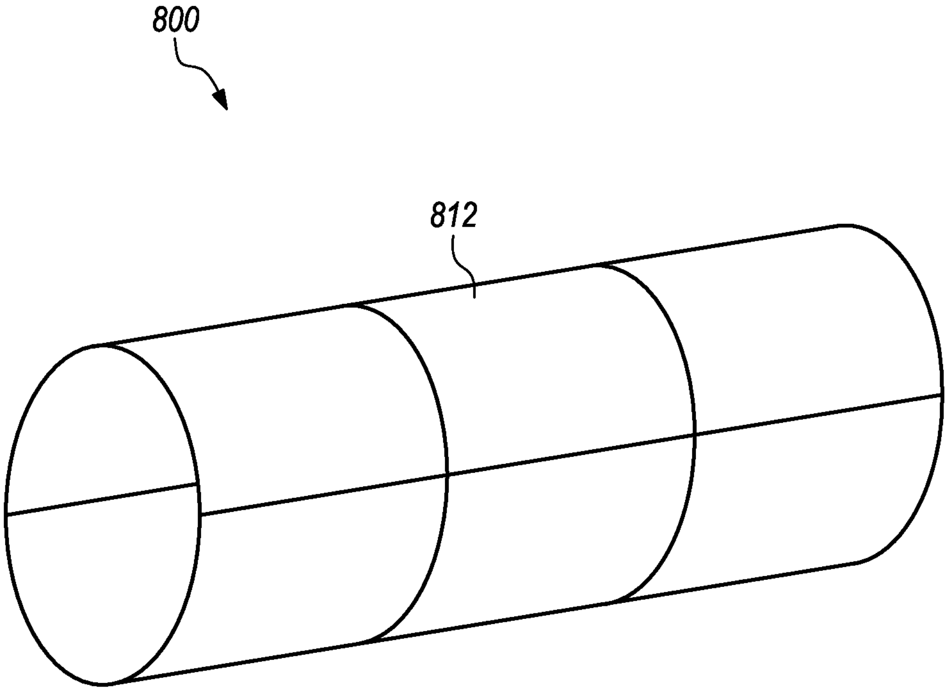
FIG. 8 is a simplified perspective view of still yet another embodiment of the locator assembly.

FIG. 8 is a simplified perspective view of still yet another embodiment of the locator assembly 800. In this embodiment, the locator assembly 800 simply includes a device body 812, such as the self-expanding device body 512 illustrated and described in detail above in relation to FIGS. 5A-5C and/or the self-expanding device body 612 illustrated and described in detail above in relation to FIG. 6. In particular, the device body 812 can include and/or incorporate a spontaneous, passive, self-expanding, lattice-like structural design that is configured to function as a typical stent device in any suitable locations within the body of the patient. More specifically, it is noted that the locator assembly 800 does not include the plurality of electrodes 102 (illustrated in FIG. 1A) or the communicator 404 (illustrated in FIG. 4), which were included in certain previous embodiments. Thus, without the plurality of electrodes 102, it is appreciated that this embodiment of the locator assembly 800 would not specifically include the capabilities for locating arrhythmogenic foci 732 (illustrated in FIG. 7) in or near the heart 701 (illustrated in FIG. 7), but would rather function as a stent for purposes of holding open whatever vessel of the body of the patient in which the locator assembly 800 is deployed. For this reason, in this embodiment, the locator assembly 800 may also sometimes be referred to as a "stent assembly".

It is appreciated that the locator assembly 800 and/or the device body 812 can be deployed in any desired locations within the body of the patient using any suitable deployment catheter, such as the deployment catheter 524 illustrated and described above in relation to the embodiment shown in FIGS. 5A-5C and/or the deployment catheter 624 illustrated and described above in relation to the embodiment shown in FIG. 6. As above, the locator assembly 800 and/or the device body 812 will typically be positioned fully within the inner cavity 523A (illustrated, for example, in FIG. 5A) of the sheath 523 (illustrated, for example, in FIG. 5A) of the deployment catheter 524 (illustrated, for example, in FIG. 5A), and/or fully within the inner cavity 623A (illustrated in FIG. 6) of the sheath 623 (illustrated in FIG. 6) of the deployment catheter 624 (illustrated in FIG. 6), during initial deployment of the locator assembly 800. When so positioned fully within the inner cavity 523A, 623A of the sheath

523, 623 the locator assembly 800 and/or the device body 812 will be in the contracted state, as the structure of the sheath 523, 623 will compress the locator assembly 800 into a more compact configuration, and inhibit the locator assembly 800 and/or the device body 812 from moving to the expanded state. Subsequently, the sheath 523, 623 can be moved and/or retracted relative to the locator assembly 800 so that the locator assembly 800 and/or the device body 812 can spontaneously expand to the expanded state, and be positioned at the desired location within the body of the patient. Thus, the locator assembly 800 and/or the device body 812 can function solely as a typical stent device at the desired location within the body of the patient.

It is appreciated that this embodiment of the locator assembly 800 can have any suitable design for purposes of maintaining the locator assembly 800 and/or the device body 812 in engagement with the inner cavity 523A, 623A of the sheath 523, 623 during full use of the locator assembly 800 within the body of the patient. For example, the locator assembly 800 can further utilize (i) the tethering system 521 (illustrated in FIG. 5C) in order to tether the locator assembly 700 and/or the device body 712 to the inner cavity 523A of the sheath 523 of the deployment catheter 524, and/or (ii) the release inhibitor 626 (illustrated in FIG. 6) for inhibiting the locator assembly 800 and/or the device body 812 from being fully released from the within the inner cavity 623A (illustrated in FIG. 6) of the sheath 623 (illustrated in FIG. 6). Thus, with the tethering system 521 and/or the release inhibitor 626 illustrated and described herein, it is further appreciated that the locator assembly 800 and/or the device body 812 will still remain engaged with the inner cavity 523A, 623A of the sheath 523, 623 even when the locator assembly 800 and/or the device body 812 is positioned at least in part outside the inner cavity 523A, 623A of the sheath 523, 623 and is functioning as a stent to expand and/or hold open the vessel within the body of the patient while it is so deployed. With such design, upon completion of a procedure for which the locator assembly 800 is used solely as a stent, the sheath 523, 623 can again be moved relative to the locator assembly 800 so that the locator assembly 800 and/or the device body 812 gradually moves back into the inner cavity 523A, 623A of the sheath 523, 623. As the locator assembly 800 and/or the device body 812 moves back into the inner cavity 523A, 623A of the sheath 523, 623, the locator assembly 800 and/or the device body 812 will move back toward the contracted state. Subsequently, once the locator assembly 800 and/or the device body 812 has moved fully back into the inner cavity 523A, 623A of the sheath 523, 623, and the locator assembly 800 and/or the device body 812 is now fully in the contracted state, the deployment catheter 524, 624 can be used to retrieve or remove the locator assembly 800 from within the body of the patient.

Figure 9:
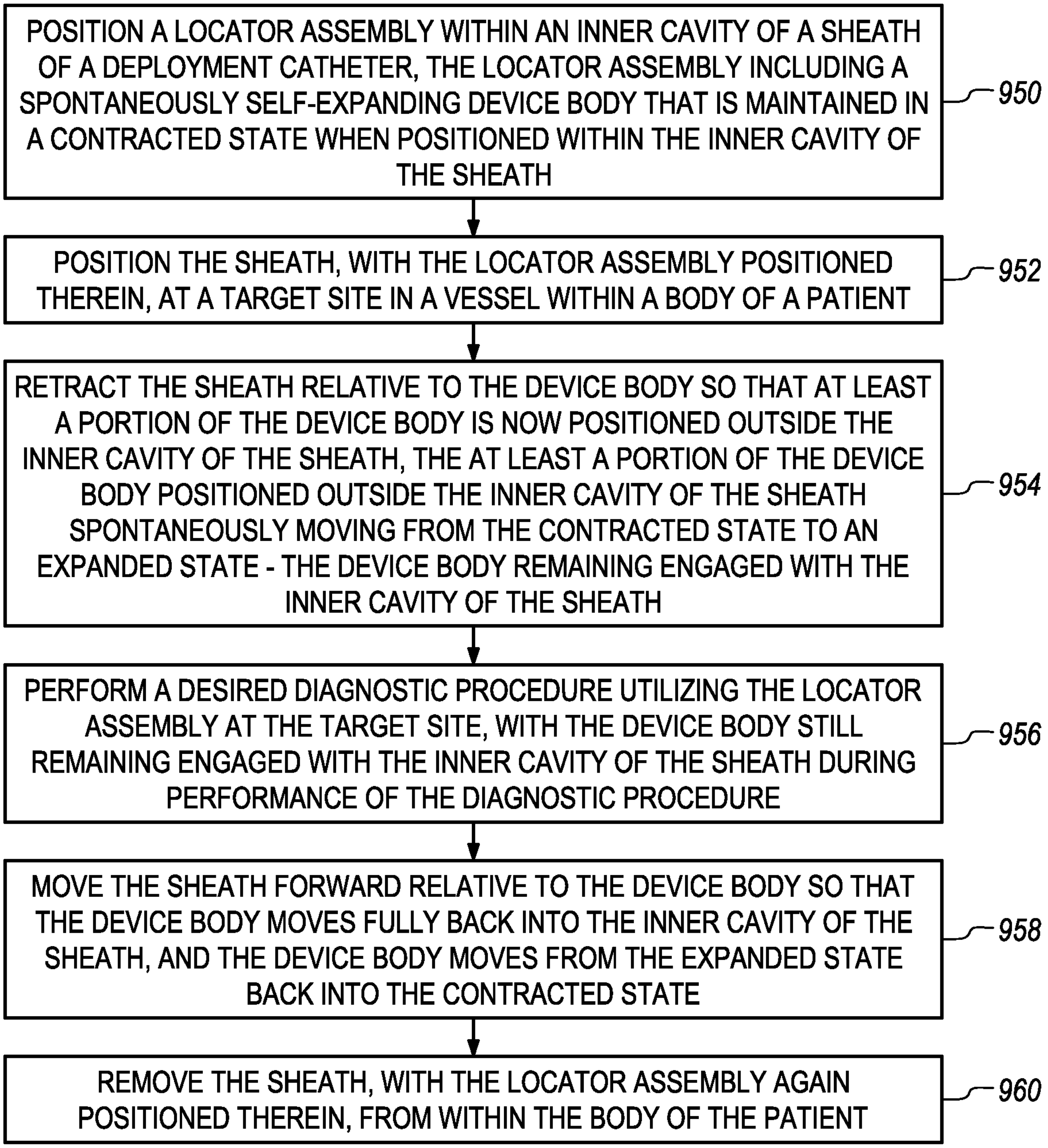
FIG. 9 is simplified flowchart illustrating an embodiment of a method for deploying and subsequently removing the locator assembly from within a body of a patient.

FIG. 9 is simplified flowchart illustrating an embodiment of a method for deploying and subsequently removing a device, such as the locator assembly, from a vessel within a body of a patient, with the locator assembly remaining engaged with the deployment catheter during the entirety of the diagnostic procedure. It is understood that the method pursuant to the disclosure herein can include greater or fewer steps than those shown and described relative to FIG. 9. The method can omit one or more steps illustrated in FIG. 9. The method can add additional steps not shown and described in FIG. 9, and still fall within the purview of the present invention. Further, the sequence of the steps can be varied from those shown and described relative to FIG. 9. The sequence of steps illustrated in FIG. 9 is not intended to limit the sequencing of steps in any manner.

In the embodiment illustrated in FIG. 9, at step 950, a locator assembly is positioned within an inner cavity of a sheath of a deployment catheter. The locator assembly includes at least a device body. In many embodiments, the device body includes a spontaneous, passive, self-expanding, lattice-like structural design that is configured to spontaneously move from a contracted state to an expanded state when any contracting force that is otherwise exerted onto the device body is removed. Thus, it is appreciated that the physical structure of the sheath provides a force onto the device body of the locator assembly so that the device body remains in the contracted state when the locator assembly and/or device body is positioned within the inner cavity of the sheath.

At step 952, the sheath, with the locator assembly positioned therein, is positioned at a target site in a vessel within a body of a patient.

At step 954, the sheath is retracted relative to the locator assembly and/or the device body so that at least a portion of the locator assembly and/or the device body is now positioned outside the inner cavity of the sheath. The at least a portion of the locator assembly and/or the device body now positioned outside the inner cavity of the sheath spontaneously moves from the contracted state to the expanded state. The at least a portion of the locator assembly is thus positioned in the expanded state at the target site in the vessel within the body of the patient. It is appreciated that the locator assembly and/or the device body remains engaged with the inner cavity of the sheath even though a portion or all of the locator assembly and/or the device body is now positioned outside the inner cavity of the sheath. As described herein, the locator assembly and/or the device body can remain engaged with the inner cavity of the sheath due to any suitable design modifications of the locator assembly and/or the deployment catheter, such as through the use of a tethering system that is coupled to the locator assembly and/or the device body, or a removal inhibitor that can be incorporated into the sheath and/or the device body, in certain non-exclusive embodiments.

At step 956, a desired diagnostic procedure is performed utilizing the locator assembly at the target site. It is again appreciated that the locator assembly and/or the device body remains engaged with the inner cavity of the sheath during performance of the diagnostic procedure, even if the entirety of the device body is now positioned outside the inner cavity of the sheath.

At step 958, the sheath is moved forward relative to the locator assembly and/or the device body so that the locator assembly and/or the device body moves fully back into the inner cavity of the sheath. As the locator assembly and/or the device body moves fully back into the sheath, the locator assembly and/or the device body moves from the expanded state back into the contracted state. It is appreciated that the locator assembly and/or the device body remaining engaged with the inner cavity of the sheath during performance of the diagnostic procedure greatly enhances the ability of the sheath to recapture the locator assembly and/or the device body, such that the locator assembly and/or the device body can quickly and easily move back into the inner cavity of the sheath.

At step 960, the sheath, with the locator assembly again positioned therein, is removed from within the body of the patient.

The present technology provides a system, device, and method for determining the location of arrhythmogenic foci.

In various embodiments, the system, device, and method can incorporate a locator assembly with a self-expanding stent-like design that can be implanted and/or deployed at a designated target in or near the heart for purposes of determining the location of the arrhythmogenic foci. In certain embodiments, the locator assembly can remain engaged with the deployment catheter and/or the sheath (such as with the inner cavity of the sheath) that has been used for deployment such that the locator assembly can be quickly and easily retrieved or removed from the heart of the patient after performance of the desired diagnostic procedure.

It is appreciated that the system, device, and method provided herein address multiple potential issues with the performance, reliability, and proper usage of deliverable locator assemblies, in particular locator assemblies that utilize a plurality of bipolar electrodes to determine the location of the focal point of atrial fibrillation. Specific problems solved by the system, device, and method disclosed herein include:

1) The technology disclosed herein improves the deliverable locator technology to enable mapping of precipitating episodes of clinical atrial fibrillation during the patient's daily life;
2) The technology disclosed herein increases the accuracy of the determination of the location of the focal point of atrial fibrillation;
3) The technology disclosed herein reduces the time to determine the location of the focal point of atrial fibrillation;
4) The technology disclosed herein provides for quick and easy positioning and deployment of the locator assembly at a designated target site within the patient; and
5) The technology disclosed herein further provides for quick and easy removal of the locator assembly from within the patient upon completion of the desired procedure.

It should be noted that, as used in this specification and the appended claims, the singular forms "a," "an," and "the" include plural referents unless the content and/or context clearly dictates otherwise. It should also be noted that the term "or" is generally employed in its sense, including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the detailed description provided herein. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of systems, devices, and methods for determining the location of arrhythmogenic foci have been illustrated and described herein, one or more features of any one embodiment can be combined with one or more features of one or more of the other embodiments, provided that such combination satisfies the intent of the present invention.

While a number of exemplary aspects and embodiments of the systems, devices, and methods for determining the location of arrhythmogenic foci have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A method for deploying a locator assembly in or near a heart, the method comprising the steps of:

coupling a plurality of electrodes to a device body to form at least a portion of the locator assembly, the device body including a self-expandable stent;

positioning the device body with the plurality of electrodes coupled thereto within an inner cavity of a sheath;

inserting the locator assembly within the heart while the device body is positioned within the inner cavity of the sheath;

generating relative movement between the locator assembly and the sheath so that at least a portion of the device body is no longer positioned within the inner cavity of the sheath, the device body being engaged with the inner cavity of the sheath when the at least a portion of the device body is no longer positioned within the inner cavity of the sheath;

receiving electrical signals from the heart with the plurality of electrodes of the locator assembly;

determining a location of arrhythmogenic foci in or near the heart with the locator assembly based at least in part on the electrical signals received from the heart by the plurality of electrodes, the device body remaining engaged with the inner cavity of the sheath while the locator assembly is being used to determine the location of the arrhythmogenic foci; and inhibiting the device body from being fully removed from the inner cavity of the sheath with a removal inhibitor while relative movement is generated between the locator assembly and the sheath.

2. The method of claim 1 further comprising the step of tethering the device body to the sheath with a tethering system so that the device body is tethered to the sheath when the at least a portion of the device body is no longer positioned within the inner cavity of the sheath, the tethering system being coupled to the device body and extending into the sheath.

3. The method of claim 2 wherein the step of generating includes generating relative movement between the locator assembly and the sheath so that an entirety of the device body is no longer positioned within the inner cavity of the sheath;

and wherein the step of tethering includes the device body being tethered to the sheath with the tethering system when the entirety of the device body is no longer positioned within the inner cavity of the sheath.

4. The method of claim 3 wherein the step of tethering includes coupling one or more tethering wires to the device body, and extending the one or more tethering wires into the sheath.

5. The method of claim 1 wherein the step of generating includes the at least a portion of the device body being configured to spontaneously move from a contracted state to an expanded state when the at least a portion of the device body is no longer positioned within the inner cavity of the sheath.

6. The method of claim 5 wherein the step of positioning includes the sheath being configured to maintain the device body in the contracted state while the device body is positioned within the inner cavity of the sheath.

7. The method of claim 5 further comprising the step of subsequently generating relative movement between the locator assembly and the sheath so that the at least a portion of the device body is moved back within the inner cavity of the sheath and the at least a portion of the device body moves from the expanded state back into the contracted state.

8. The method of claim 7 further comprising the step of removing the locator assembly from within the heart while the device body is positioned back within the inner cavity of the sheath.

9. The method of claim 1 wherein the step of coupling the plurality of electrodes includes positioning at least two of the plurality of electrodes circumferentially about the device body; and positioning at least two of the plurality of electrodes longitudinally along the device body.

10. The method of claim 1 further comprising the steps of electrically coupling the device body to an external device with one or more wires; and transmitting information and data from the locator assembly to the external device via the one or more wires.

11. The method of claim 1 further comprising the steps of coupling a communicator to the device body; electrically coupling the device body to an external device with the communicator; and wirelessly transmitting information and data from the locator assembly to the external device via the communicator.

12. A locator system configured for deployment in or near a heart, the locator system comprising:

a deployment catheter including a sheath that defines an inner cavity therein;

a locator assembly including (i) a device body including a self-expandable stent that is configured to be positioned within and engage the heart, the device body being positioned within the inner cavity of the sheath while the device body is being positioned within the heart; and (ii) a plurality of electrodes that are coupled to the device body, the plurality of electrodes being configured to receive electrical signals from the heart to determine a location of arrhythmogenic foci in or near the heart; and a removal inhibitor that inhibits the device body from being fully removed from the inner cavity of the sheath while relative movement is generated between the locator assembly and the sheath;

wherein relative movement between the locator assembly and the sheath is generated so that at least a portion of the device body is no longer positioned within the inner cavity of the sheath during a procedure when the locator assembly is being used to determine the location of the arrhythmogenic foci, the device body being engaged with the inner cavity of the sheath when the at least a portion of the device body is no longer positioned within the inner cavity of the sheath; and wherein the locator assembly remains engaged with the inner cavity of the sheath during the procedure when the locator assembly is being used to determine the location of the arrhythmogenic foci.

13. The locator system of claim 12 wherein the device body is tethered to the sheath with a tethering system so that the device body is tethered to the sheath when the at least a portion of the device body is no longer positioned within the inner cavity of the sheath, the tethering system including one or more tethering wires that are coupled to the device body and extend into the sheath.

14. The locator system of claim 12 wherein the sheath is configured to maintain the device body in a contracted state while the device body is positioned within the inner cavity of the sheath; and wherein the at least a portion of the device body is configured to spontaneously move from the contracted state to an expanded state when the at least a portion of the device body is no longer positioned within the inner cavity of the sheath.

15. The locator system of claim 14 wherein relative movement between the locator assembly and the sheath is subsequently generated so that the at least a portion of the device body is moved back within the inner cavity of the sheath and the at least a portion of the device body moves from the expanded state back into the contracted state; and wherein the locator assembly is removed from within the heart while the device body is positioned back within the inner cavity of the sheath.

16. The locator system of claim 12 wherein the device body is electrically coupled to an external device with one or more wires so that information and data is transmitted from the locator assembly to the external device.

17. The locator system of claim 12 wherein the locator assembly further includes a communicator that is coupled to the device body; and wherein the device body is wirelessly coupled to an external device via the communicator so that information and data is transmitted from the locator assembly to the external device.

18. A method for deploying a locator assembly in or near a heart, the method comprising the steps of:

coupling a plurality of electrodes to a device body to form at least a portion of the locator assembly, the device body including a self-expandable stent;

positioning the device body with the plurality of electrodes coupled thereto within an inner cavity of a sheath, the sheath being configured to maintain the device body in a contracted state while the device body is positioned within the inner cavity of the sheath;

inserting the locator assembly within the heart while the device body is positioned within the inner cavity of the sheath;

generating relative movement between the locator assembly and the sheath so that at least a portion of the device body is no longer positioned within the inner cavity of the sheath, the device body being engaged with the inner cavity of the sheath when the at least a portion of the device body is no longer positioned within the inner cavity of the sheath, the at least a portion of the device body being configured to spontaneously move from the contracted state to an expanded state when the at least a portion of the device body is no longer positioned within the inner cavity of the sheath, the device body being engaged with the inner cavity of the sheath via one of (i) a tethering system including one or more tethering wires that are coupled to the device body and extend into the sheath, and (ii) a removal inhibitor that inhibits the device body from being fully removed from the inner cavity of the sheath;

receiving electrical signals from the heart with the plurality of electrodes of the locator assembly;

determining a location of arrhythmogenic foci in or near the heart with the locator assembly based at least in part on the electrical signals received from the heart by the plurality of electrodes, the device body remaining engaged with the inner cavity of the sheath while the locator assembly is being used to determine the location of the arrhythmogenic foci;

subsequently generating relative movement between the locator assembly and the sheath so that the at least a portion of the device body is moved back within the inner cavity of the sheath and the at least a portion of the device body moves from the expanded state back into the contracted state; and removing the locator assembly from within the heart while the device body is positioned back within the inner cavity of the sheath.

* * * * *